United States Patent [19]

Fernandez et al.

[11] Patent Number: 5,643,247

[45] Date of Patent: Jul. 1, 1997

[54] MICROPARTICLE SWITCHING DEVICES FOR USE IN IMPLANTABLE RESERVOIRS

[75] Inventors: Julio M. Fernandez, Rochester, Minn.; Chaya Nanavati, Cary, N.C.

[73] Assignee: Mayo Foundation for Medical Education and Research, Rochester, Minn.

[21] Appl. No.: 249,435

[22] Filed: May 26, 1994

Related U.S. Application Data

[63] Continuation-in-part of Ser. No. 7,328, Jan. 21, 1993, abandoned and a continuation-in-part of PCT/US94/00788, Jan. 21, 1994.

[51] Int. Cl.⁶ .................................................. A61K 9/22
[52] U.S. Cl. ........................ 604/891.1; 604/93; 604/250
[58] Field of Search ............................ 604/890.1–892.1, 604/20, 30, 31, 65, 93, 126, 153, 169, 190, 215, 245, 246, 256, 250; 137/909; 251/129.01, 129.06

[56] References Cited

U.S. PATENT DOCUMENTS

| | | |
|---|---|---|
| 4,140,121 | 2/1979 | Kuhl et al. . |
| 4,140,122 | 2/1979 | Kuhl et al. . |
| 4,577,642 | 3/1986 | Stokes . |
| 4,581,624 | 4/1986 | O'Connor ............................ 357/26 |
| 4,639,244 | 1/1987 | Rizk et al. . |
| 4,705,503 | 11/1987 | Dorman et al. . |
| 4,787,888 | 11/1988 | Fox . |
| 4,871,680 | 10/1989 | Barraud et al. . |
| 4,873,088 | 10/1989 | Mayhew et al. . |
| 4,886,514 | 12/1989 | Maget . |
| 4,895,719 | 1/1990 | Radhakrishnan et al. . |
| 4,912,032 | 3/1990 | Hoffman et al. . |
| 5,008,102 | 4/1991 | York . |
| 5,008,253 | 4/1991 | Casu et al. . |
| 5,019,372 | 5/1991 | Folkinen et al. . |
| 5,041,107 | 8/1991 | Heil, Jr. . |
| 5,062,841 | 11/1991 | Siegel . |
| 5,152,758 | 10/1992 | Kaetsu et al. . |
| 5,171,578 | 12/1992 | Bally et al. . |
| 5,188,826 | 2/1993 | Chandrasekaran et al. . |
| 5,192,535 | 3/1993 | Davis et al. . |
| 5,226,902 | 7/1993 | Bae et al. ............................ 604/891.1 |
| 5,240,713 | 8/1993 | Ayer .................................... 604/891.1 |
| 5,336,057 | 8/1994 | Fukuda et al. ...................... 417/395 |
| 5,400,824 | 3/1995 | Gschwendtner et al. ........... 137/625.28 |
| 5,417,235 | 5/1995 | Wise et al. ......................... 137/1 |
| 5,452,878 | 9/1995 | Gravesen et al. .................. 251/129.02 |

FOREIGN PATENT DOCUMENTS 86-051826   6/1984   European Pat. Off. .

OTHER PUBLICATIONS

Abe, T., et al., "Synthesis and Characterization of Thermo–Sensitive Polymeric Beads," *Journal of Applied Polymer Science* 40: 1223–1235 (1990).

Aitken, M.L., and P. Verdugo, "Donnan mechanism of mucin release and conditioning in goblet cells: the role of polyions," *Soc. Exp. Biol.*: 73–80 (1989).

Annaka, M., and T. Tanaka, "Multiple phases of polymer gels," *Nature* 355: 430–432 (1992).

Arshady, R., "Microspheres for biomedical applications: preparation of reactive and labelled microspheres," *Biomaterials* 14(1): 5–15 (1993).

Atkins, T.W., et al., "Incorporation and release of fluorescein isothiocyanate–linked dextrans from a bead–formed macroporous hydrophilic matrix with potential for sustained release," Biomaterials 14(1): 16–20 (1993).

Breckenridge, L.J., and W. Almers, "Currents through the fusion pore that forms during exocytosis of a secretory vesicle," *Nature* 328: 814–817 (1987).

(List continued on next page.)

*Primary Examiner*—Mark Bockelman
*Attorney, Agent, or Firm*—Peter J. Dehlinger; LeeAnn Gorthey

[57] ABSTRACT

A diode device (10) containing a microparticle polymer element (12) is described. Also described are mechanical switching devices that employ the microparticle polymer element.

11 Claims, 14 Drawing Sheets

OTHER PUBLICATIONS

Breckenridge, L.J., and W. Almers, "Final steps in exocytosis observed in a cell with giant secretory granules," *Proc. Natl. Acad. Sci. USA* 84: 1945–1949 (1987).

Candau, F., et al., "Kinetic Study of the Polymerization of Acrylamide in Inverse Microemulsion," *J. Poly Sci.* Part A, 23: 193–214 (1985).

Chevalier, P., et al., "Comparative study on the diffusion of an IgG from various hydrogel beads," *Biotechnology Techniques* 1(3): 201–206 (1987).

Clark, A.H., and S.B. Ross–Murphy, "Structural and mechanical properties of biopolymer gels," *Adv. in Polymer Sci.* 83: 57–142 (1987).

Curran, M.J., and M.S. Brodwick, "Ionic Control of the Size of the Vesicle Matrix of Beige Mouse Mast Cells," *J. Gen. Physiol.* 98: 771–790 (1991).

Duzgunes, N., and P.L. Felgner, "Intracellular Delivery of Nucleic Acids and Transcription Factors by Cationic Liposomes," *Methods in Enzymology* 221: 303–306 (1993).

Edwards, S.F., "Sixth International Congress of Biorheology Plenary Lecture: The Theory of Macromolecular Networks," *Biorheology* 23: 589–603 (1986).

Fernandez, J.M., et al., "Reversible condensation of mast cell secretory products in vitro," *Biophys. J.* 59: 1022–1027 (1991).

Fujimoto, K., et al., "Interactions between Thermosensitive Hydrogel Microspheres and Proteins," *Journal of Intelligent Material Systems and Structures* 4: 184–189 (1993).

Fujimoto, K., et al., "Fluorescence Analysis for Thermosensitive Hydrogel Microspheres," *Polymer International* 30: 237–241 (1993).

Gehrke, S.H., and E.L. Cussler, "Mass transfer in pH–sensitive hydrogels," *Chem. Eng. Sci.* 44: 559–566 (1989).

Hoffman, A.S., "Thermally reversible hydrogels containing biologically active species," in *Polymers in Med. III* (Migliarese, C., et al., eds., Elsevier Sci. Pub., Amsterdam, pp. 161–167, 1988).

Hoffman, A.S., "Molecular Bioengineering of Biomaterials in the 1990s and Beyond: A Growing Liaison of Polymers with Molecular Biology," *Artificial Organs* 16(1): 43–49 (1992).

Hoffman, A.S., "Environmentally Sensitive Polymers and Hydrogels. Smart Biomaterials," *MRS Bulletin* Sep.: 42–46 (1991).

Hoffman, A.S., "Applications of Thermally Reversible Polymers and Hydrogels in Therapeutics and Diagnostics," *Journal of Controlled Release* 6: 297–305 (1987).

Hoke, F., "'Smart' Materials Research Expands Beyond Defense Arena," *The Scientist*, Apr. 27: 13 (1992).

Huang, Y., et al., "Synthesis and characterization of bisacrylamide microgels containing sulfo groups," *Makromol. Chem.* 186: 273–281 (1985).

Ilmain, F., et al., "Volume transition in a gel driven by hydrogen bonding," *Nature* 349: 400–401 (1991).

Ishihara, K., et al., "Controlled release of organic substances using polymer membrane with responsive function for amino compounds," *J. Appl. Polym. Sci.* 29: 211–217 (1984).

Kajiwara, K., and S.B. Ross–Murphy, "Synthetic gels on the move," *Nature* 355: 208–209 (1992).

Kawaguchi, H., et al., "Preparation and Modification of Monodisperse Hydrogel Microspheres," *Polymer International* 30: 225–231 (1993).

Kerkam, K., et al., "Liquid crystallinity of natural silk secretions," *Nature* 349: 596–598 (1991).

Kibat, P.G., et al., "Enzymatically activated microencapsulated liposomes can provide pulsatile drug release," *The FASEB Journal* 4: 2533–2539 (1990).

Kim, T.D., et al., "Studies on Liposome–Encapsulated Heparin," *Thrombosis Research* 43: 603–612 (1986).

Kishi, R., and Y. Osada, "Reversible Volume Change of Microparticles in an Electric Field," *J. Chem. Soc., Faraday Trans.* 1, 85(3): 655–662 (1989).

Klein, J., et al., "Forces between polymer–bearing surfaces undergoing shear," *Nature* 352: 143–145 (1991).

Kokufata, E., et al., "Saccharide–sensitive phase transition of a lectin–loaded gel," *Nature* 351: 302–304 (1991).

Kreuter, J., "Nanoparticles—Preparation and Applications," Chapter 6 from *Microcapsules and Nanoparticles in Medicine and Pharmacy* (M. Donbrow, ed., CRC Press Florida, 1992, pp. 125–148 ).

Kuhn, W., et al., "Reversible dilation and contraction by changing the state of ionization of high–polymer acid networks," *Nature* 165: 514–516 (1950).

Kwon, I.C., et al., "Electrically erodible polymer gel for controlled release of drugs," *Nature* 354: 291–293 (1991).

Kwon, G.S., et al., "Release of proteins via ion exchange from albumin–heparin microspheres," *Journal of Controlled Release* 22: 83–94 (1992).

Langer, R., "New Methods of Drug Delivery," *Science* 249: 1527–1532 (1990).

Lasic, D.D., et al., "Gelation of liposome interior. A novel method for drug encapsulation," *FEBS Letters* 312(2,3): 255–258 (1992).

Miyamoto, T., and K. Shibayama, "Free–volume model for ionic conductivity in polymers," *J. Appl. Phys.* 44(12): 5372–5374 (1973).

Monck, J.R., et al., "Is swelling of the secretory granule matrix the force that dilates the exocytotic fusion pore?" *Biophys. J.* 59: 39–47 (1992).

Nakamae, K., et al., "Swelling behavior of hydrogels containing phosphate groups," *Makromol. Chem.* 193: 983–990 (1992).

Nanavati, C., et al., "The Secretory Granule Matrix: A Fast-Acting Smart Polymer," *Science* 259: 963–965 (1993).

Nanavati, C., Doctoral Dissertation: "Excytosis: An Analysis of the Properties of the Fusion Pore and the Secretory Granule Matrix," Nov., 1992.

Okahata, Y., et al., "Thermoselective permeation from a polymer–grafted capsule membrane," *Macromolecules* 19: 493–494 (1986).

Okano, T., et al., "Thermally On–Off Switching Polymers for Drug Permeation and Release," *Journal of Controlled Release* 11: 255–265 (1990).

Okubo, M., and T. Nakagawa, "Preparation of micron–size mono–disperse polymer particles having highly crosslinked structures and vinyl groups by seeded polymerization of divinylbenzene using the dynamic swelling method," *Colloid Polym. Sci.* 270: 853–858 (1992).

Osada, Y., "Conversion of Chemical Into Mechanical Energy by Synthetic Polymers (Chemomechanical Systems)," *Advances in Polymer Science* 82: 1–46 (1987).

Osada, Y., et al., "A polymer gel with electrically driven motility," *Nature* 355: 242–244 (1992).

Ostro, M.J., and P.R. Cullis, "Use of liposomes as injectable–drug delivery systems," *American Journal of Hospital Pharmacy* 46: 1576–1587 (1989).

Park, T.G., and A.S. Hoffman, "Preparation of Large, Uniform Size Temperature-Sensitive Hydrogel Beads," *Journal of Polymer Science Part A,* vol. 30: 505–507 (1992).

Park, T.G., and A.S. Hoffman, "Immobilization of *Arthrobacter simplex* in a thermally reversible hydrogel: effect of temperature cycling on steroid conversion," *Biotech. and Bioeng.* 35: 152–159 (1990).

Pekarek, K.J., et al., "Double-walled polymer microspheres for controlled drug release," *Nature* 367: 258–260 (1994).

Pelton, R.H., "Polystyrene and Polystyrene-butadiene Latexes Stabilized by Poly (N-isopropylacrylamide)," *Journal of Polymer Science Part A,* vol. 26: 9–18 (1988).

Pelton, R.H., and P. Chibante, "Preparation of Aqueous Latices with N-Isopropylacrylamide," *Colloids and Surfaces* 20: 247–256 (1986).

Radomsky, M.L., et al., "Macromolecules released from polymers: diffusion into unstirred fluids," *Biomater.* 11: 619–624 (1990).

Siegel, R.A., and B.A. Firestone, "pH-dependent equilibrium swelling properties of hydrophobic polyelectrolyte copolymer gels," *Macromolecules* 21: 3254–3259 (1988).

Steinberg, I.Z., et al., "Mechanochemical Engines," *Nature* 210: 568–571 (1966).

Straubinger, R.M., "pH-Sensitive Liposomes for Delivery of Macromolecules into Cytoplasm of Cultured Cells," *Methods in Enzymology* 221: 361–376 (1993).

Suzuki, A., and T. Tanaka, "Phase transition in polymer gels induced by visible light," *Nature* 346: 345–347 (1990).

Tam, P.Y., and P. Verdugo, "Control of mucus hydration as a Donnan equilibrium process," *Nature* 292: 340–342 (1981).

Tanaka, T., et al., "Collapse of Gels in an Electric Field," *Science* 218: 467–469 (1982).

Tanaka, T., and D.J. Fillmore, "Kinetics of swelling of gels," *J. Chem. Phys.* 70(03): 1214–1218 (1979).

Tanaka, T., "Gels," pp. 124–138.

Tanaka, T., "Collapse of gels and the critical endpoint," *Phys. Rev. Lett.* 40: 820–823 (1978).

Tanaka, T., et al., "Phase transitions in ionic gels," *Phys. Rev. Lett.* 45: 1636–1639 (1980).

Urry, D.W., et al., "Chemical potential driven contraction and relaxation by ionic strength modulation of an inverse temperature transition," *J. Am. Chem. Soc.* 110: 3303–3305 (1988).

Verdugo, P., "Mucin Exocytosis," *American Review of Respiratory Disease* 144(3, Part 2): S33–S37 (1991).

Verdugo, P., et al., "Molecular Mechanism of Product Storage and Release in Mucin Secretion. II. The Role of Extracellular $Ca^{++}$," *Biorheology* 24: 625–633 (1987).

Weiner, A.L., et al., "Liposome-Collagen Gel Matrix: A Novel Sustained Drug Delivery System," *Journal of Pharmaceutical Sciences* 74(9): 922–925 (1985).

Williams, C., et al., "Polymer collapse," *Ann. Rev. Phys. Chem.* 32: 433–451 (1981).

Yui, N., et al., "Photo-responsive degradation of heterogeneous hydrogels comprising crosslinked hyaluronic acid and lipid microspheres for temporal drug delivery," *Journal of Controlled Release* 26: 141–145 (1993).

Yui, N., et al., "Inflammation responsive degradation of cross-linked hyaluronic acid gels," *Journal of Controlled Release* 22: 105–116 (1992).

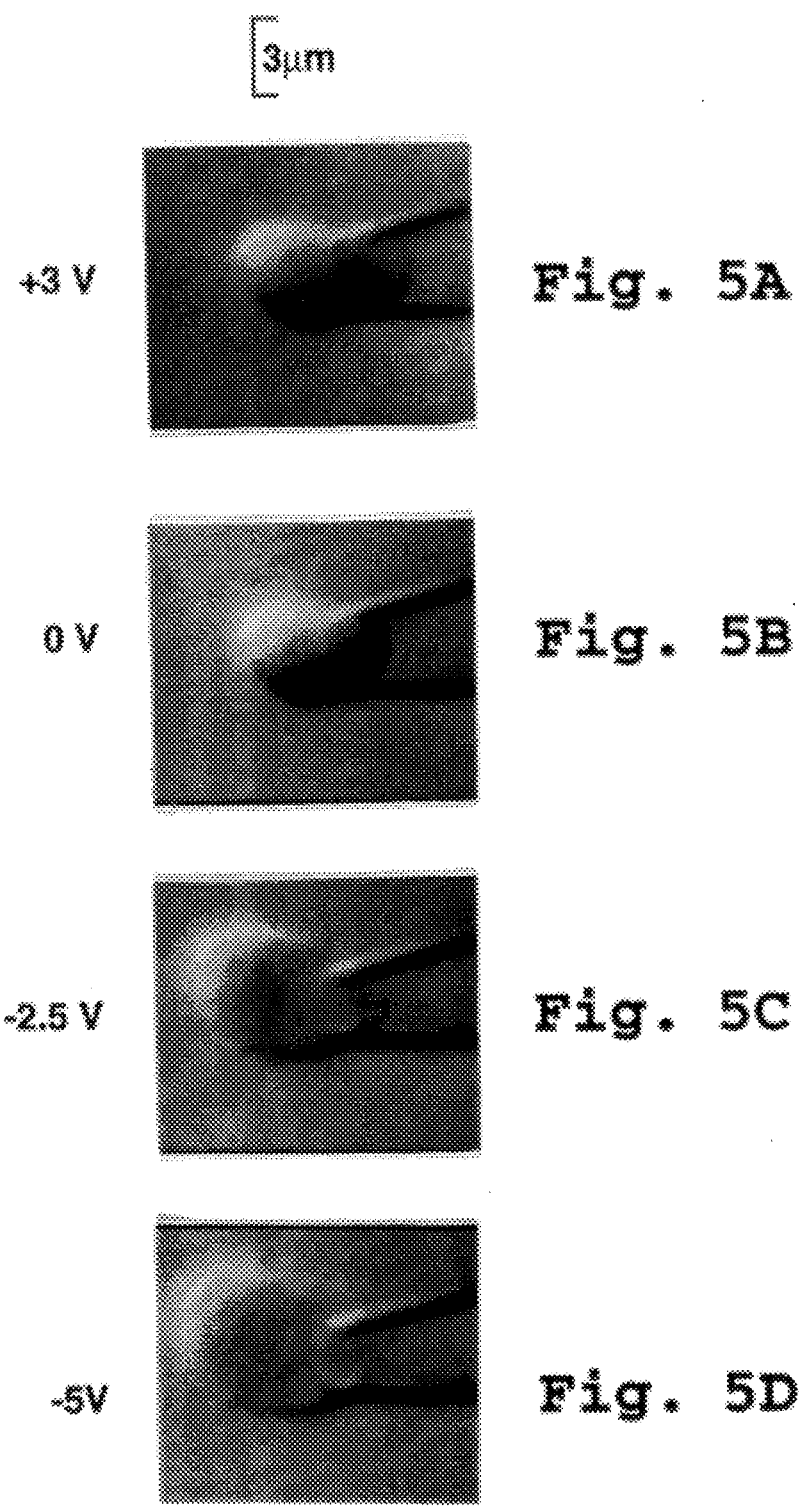

↓ UV

MICROPARTICLE SWITCHING DEVICES FOR USE IN IMPLANTABLE RESERVOIRS

The present invention is a continuation-in-part of U.S. patent application Ser. No. 08/007,328, filed Jan. 21, 1993, now abandoned, and claims the priority of the corresponding PCT patent application for "Microparticle Switch Device", filed Jan. 21, 1994, now abandoned. The present application is also a continuation-in-part of PCT/US94/00788, filed Jan. 21, 1994.

FIELD OF THE INVENTION

The present invention relates to polymer-matrix microparticles and their uses in electrical diode devices and miniature switching devices.

REFERENCES

Antonietti, M., et al., *Macromolecules*, 18:1162 (1985).
Arshady, R., *Biomaterials* 14(1):5–20 (1993).
Cadan, F., et al., *J. Poly Sci.*, Part A, 23:193 (1985).
Hosaka, S., et al., *Immunological Communications* 12(5):509–517 (1983).
Huang, Y., et al., *Makromol. Chem.*, 186:273 (1985).
Kamei, S., et al., *J. Polymer Sci.: Part A: Polymer Chem.* 24:3109–3116 (1986).
Kawaguchi, H., et al., *Polymer J.* 23(8):955–962 (1991).
Kawaguchi, H., et al., *Colloid and Polymer Sol.* (1):53 (1992).
Kawaguchi, H., et al., *Polymer Int.* 30:225–231 (1993).
Kreuter, J., in *Microcapsules and Nanoparticles in Medicine and Pharmacy*, CRC Press, Boca Raton Fla. (1992).
Margel, S., et al., *J. Cell Sci.* 56:157–175 (1982).
Okubo, M., et al., in "Production of Multihollow Polymer Particles by Stewise Alkali-Acid Method" in *Polymer Latexes* (Daniels, E. S., et al., eds.) American Chemical Society, Washington D.C. (1992).
Okubo, M., and Nakagawa, T., *Collid Polym. Sci.* 270:853–858 (1992).
Pelton, R. H., and Chibante, P., *Colloids and Surfaces* 20:247–256 (1986).
Pelton, R. H., *J. Polym. Sci.: Part A: Polym. Chem.* 26:9–18 (1988).
Tai, E. F., *J. Poly Sci.*, Part A, 24:567 (1986).
Tanaka, H., et al., *Biotech. and Bioeng.* 26:53–58 (1984).
Vanderhoff, M. S., et al., *Polym. Matr Sci Eng.*, 54:587 (1986).
Wong. S. S., *Chemistry of Protein Conjugation and Crosslinking*, CRC Press, 1991.
Yui, N., et al., *J. Controlled Rel.* 22.:105–116 (1992).

BACKGROUND OF THE INVENTION

Diodes are electronic elements capable of conducting current, in response to a voltage potential placed across the diode, in one direction only. As such, these elements are widely used in electronic applications, such as current rectification and signal gating.

Diodes may be designed to respond to various environmental conditions, such as temperature, electromagnetic radiation, or magnetic fields, and in this capacity, the diode may function as a sensor of the diode-response condition. It would be desirable to extend the range of diode response to a variety of chemical and biological conditions, such as pH, the salt concentrations, and the presence or absence of specific binding agents, such as biological analytes.

It would also be desirable to provide a miniature (micronscale) diode element capable of swelling and contracting rapidly in response to voltage changes across the element, for use in constructing miniature devices such as pumps and mechanical actuators.

SUMMARY OF THE INVENTION

The present invention includes, in one aspect, a switching device designed for use with a voltage source. The device includes a polymer-matrix microparticle composed of a matrix of crosslinked polyionic polymer filaments, a first chamber containing an electrolyte medium that is in contact with an interior surface region of the microparticles' outer surface, and an exterior chamber containing an electrolyte medium that is in contact with an exterior surface region of the microparticles' outer surface.

The configuration of the chambers is such that the interior surface region in contact with the electrolyte in the first chamber is substantially smaller than the exterior surface region in contact with the electrolyte in the second chamber, preferably at least 25–100 times smaller.

Also included are electrical connections adapted to connect the electrolyte medium in the chambers to the voltage source, to produce a voltage across the chambers of a selected voltage level and polarity. The device allows current flow between the two chambers when the voltage has one polarity, and substantially blocks current flow between the chambers when the voltage has the opposite polarity.

The aqueous electrolyte medium may contain a divalent or multivalent solute species effective to condense the microparticle, in the absence of an electric field, where the microparticle is decondensed in the presence of an electric field whose polarity is effective to allow current flow.

In one preferred embodiment, the microparticle has a dimension between about 0.5 and 5.0 μm, and the microparticle matrix is composed of crosslinked polyanionic polymer filaments, such as sulfated, sulfonated, carboxylated, or phosphated comb-polymer glycoprotein filaments.

The device may take the form of a miniature, preferably implantable machine, such as a passive-diffusion drug-delivery device, pump, or mechanical actuator.

The device may also be employed in an electronic circuit, as a diode or optical switch.

The device may also be employed as a sensor, to detect changes in electrical field, or changes related to solution parameters, such as monovalent ion concentration, pH, temperature, or the presence of biological analytes.

Figure 1:
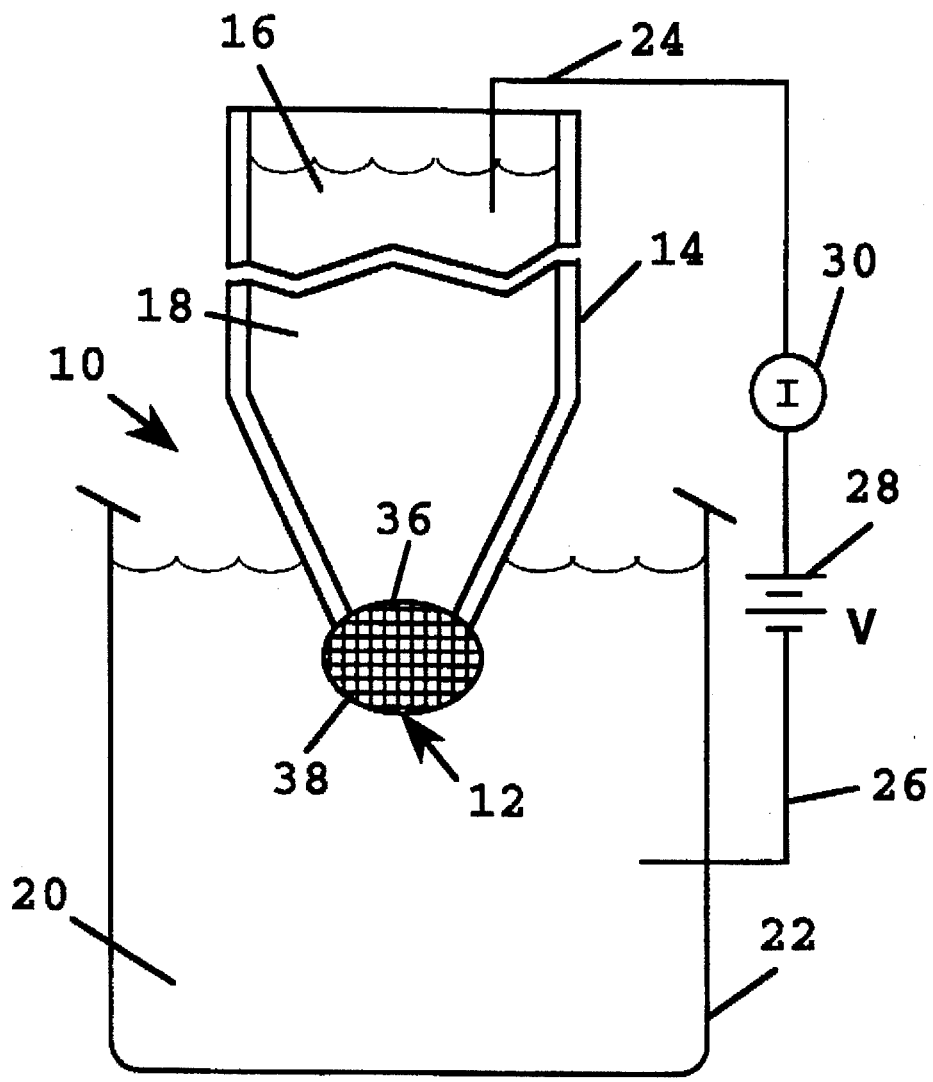
FIG. 1 shows the circuit components used for measuring changes in a charged-polymer microparticle, in response to application of an asymmetric electric field across the microparticle.
Figure 4A:
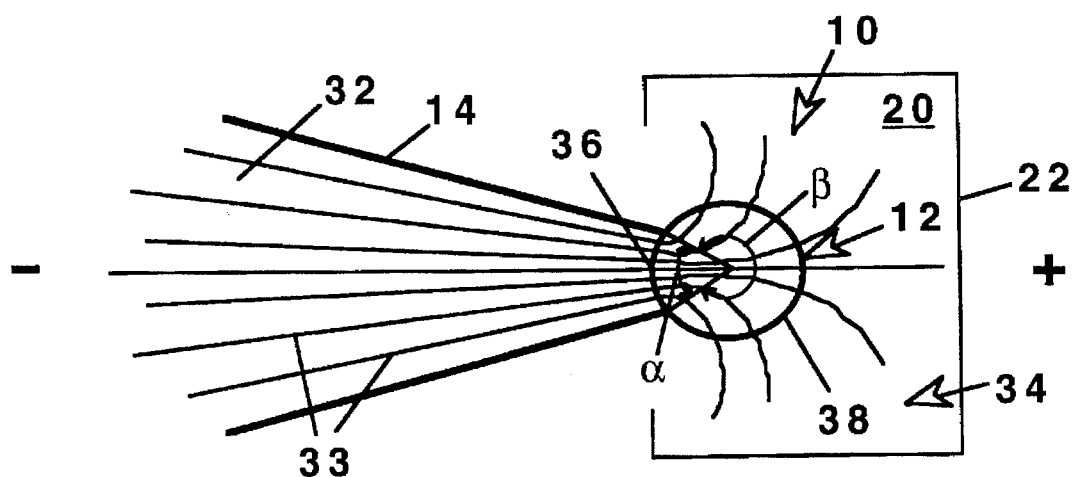
FIGS. 4A–4C illustrate the interaction of an asymmetric electric field with a charged-polymer microparticle (FIG.
Figure 4B:
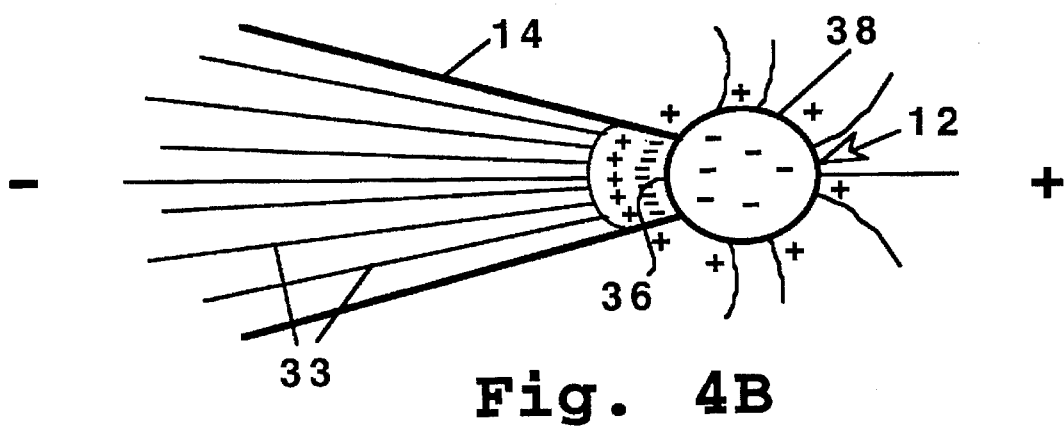
Figure 4C:
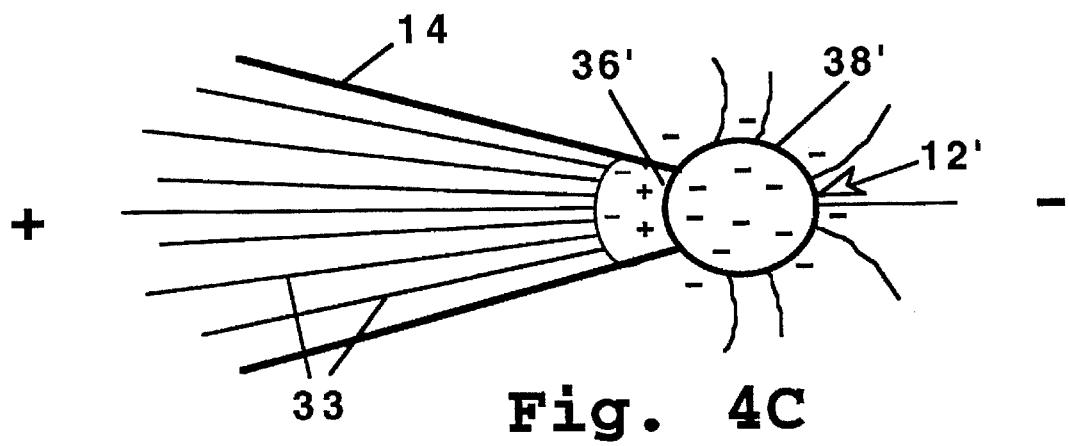
Figure 6:
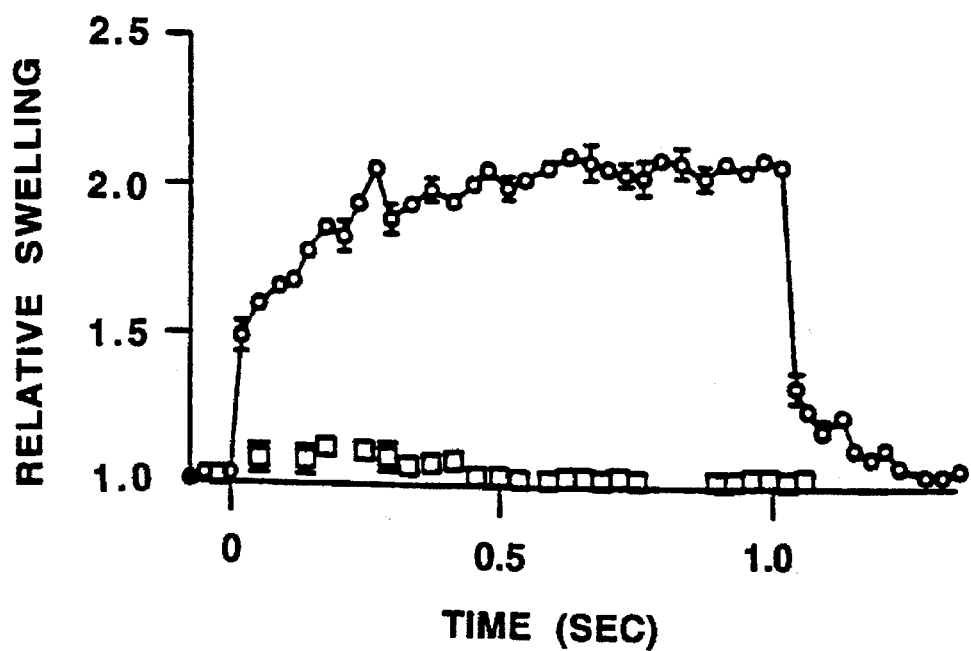
Figure 7:
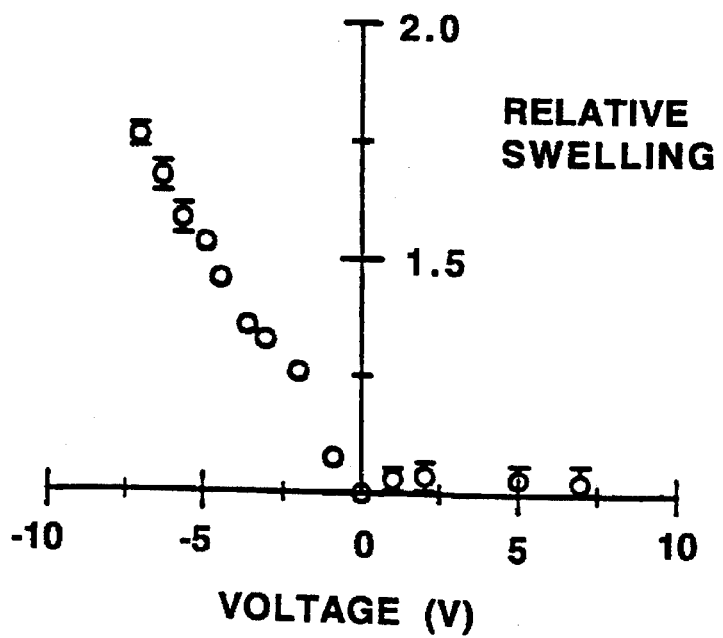
Figure 8A:
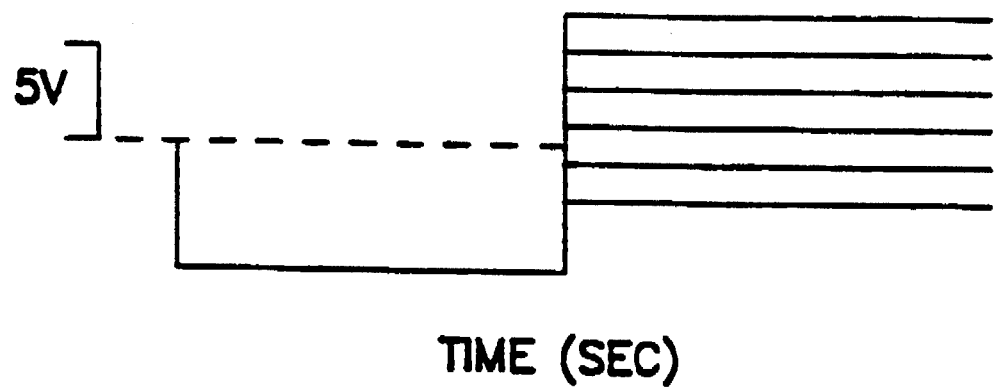
Figure 8B:
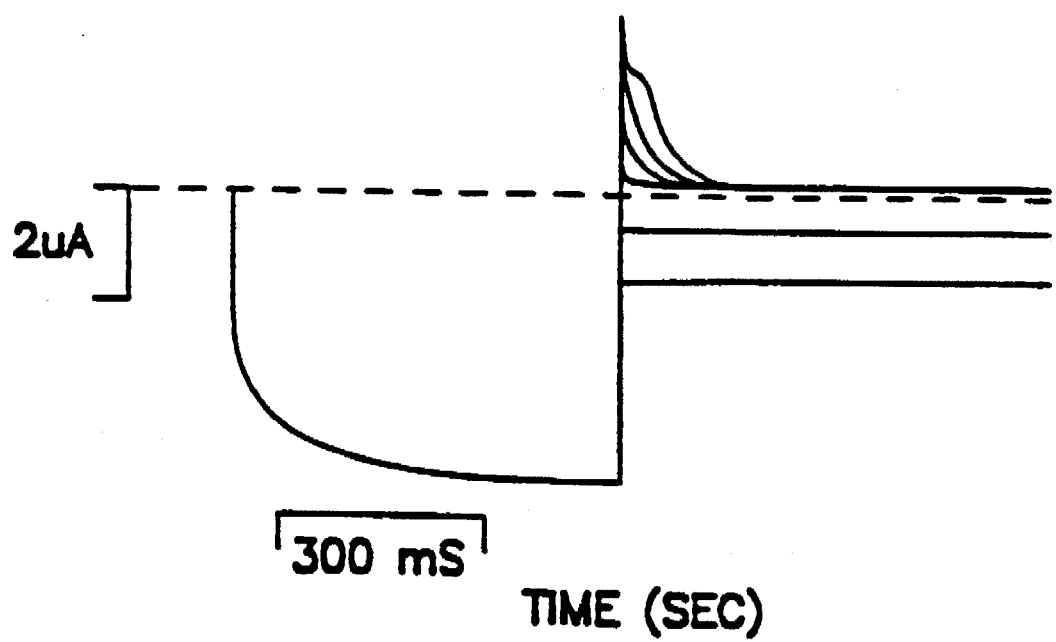
Figure 9:
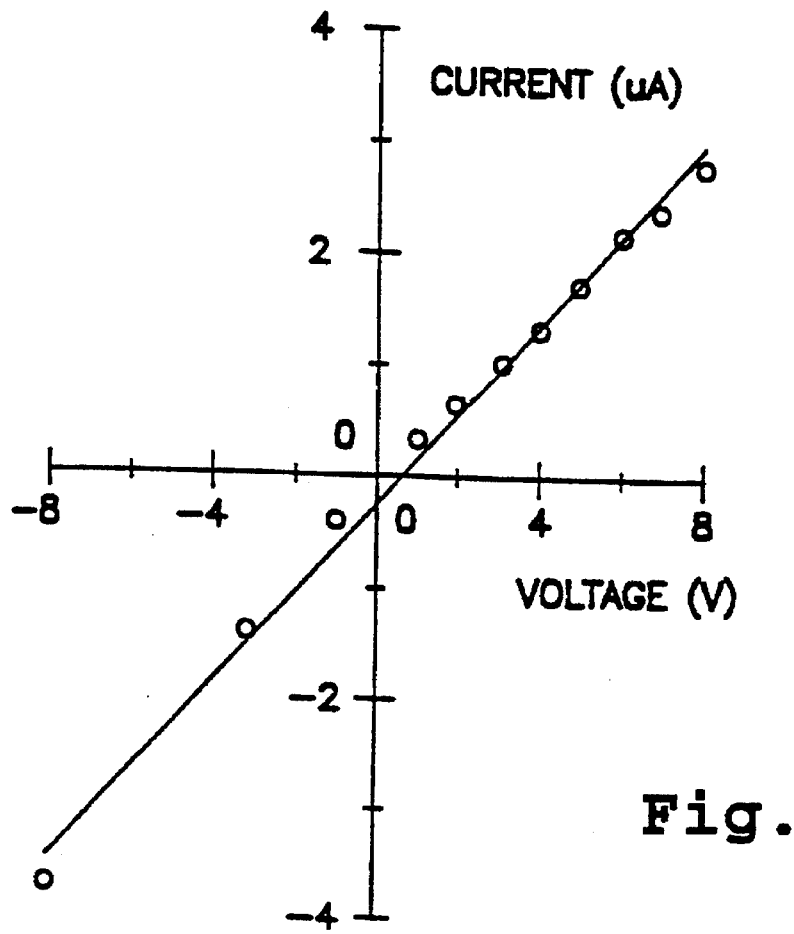
Figure 10:
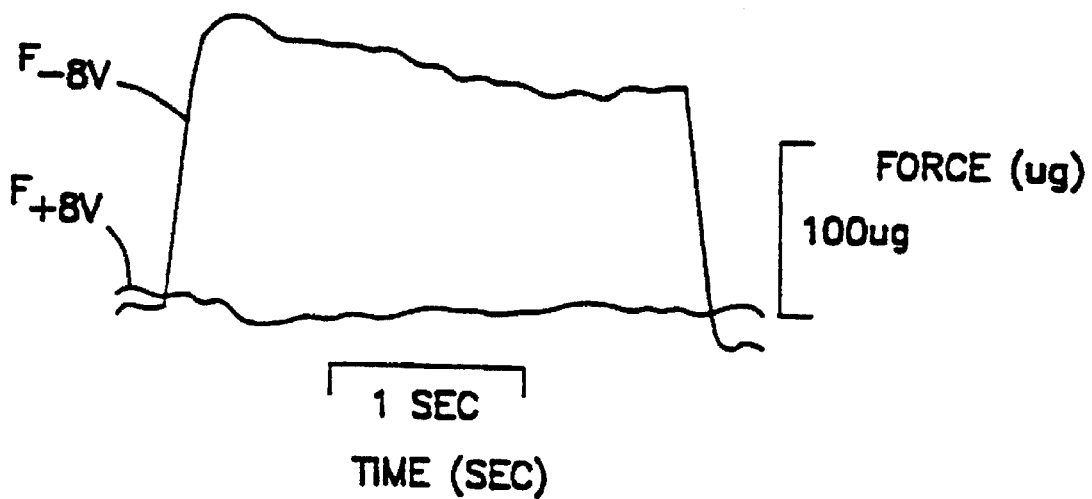
Figure 11:
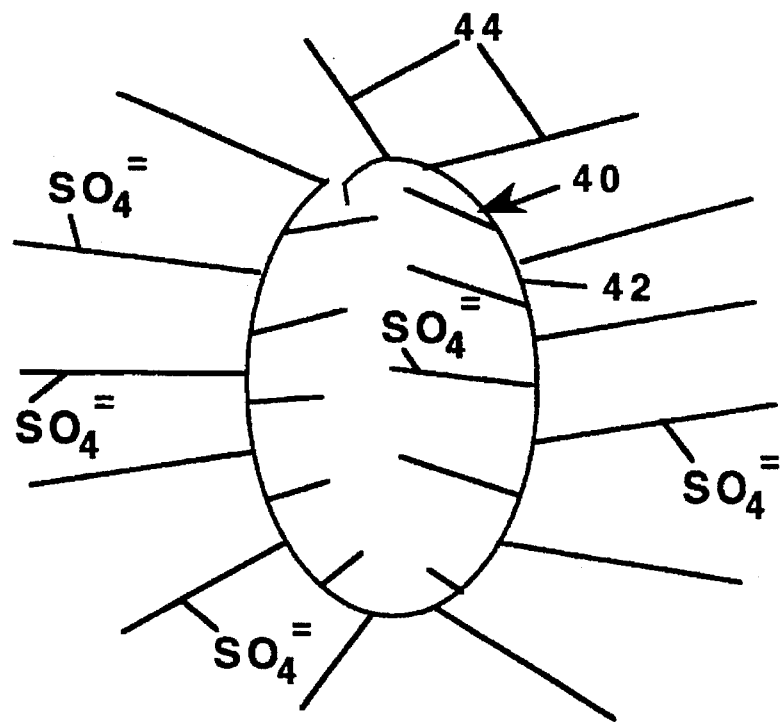
Figure 12A:
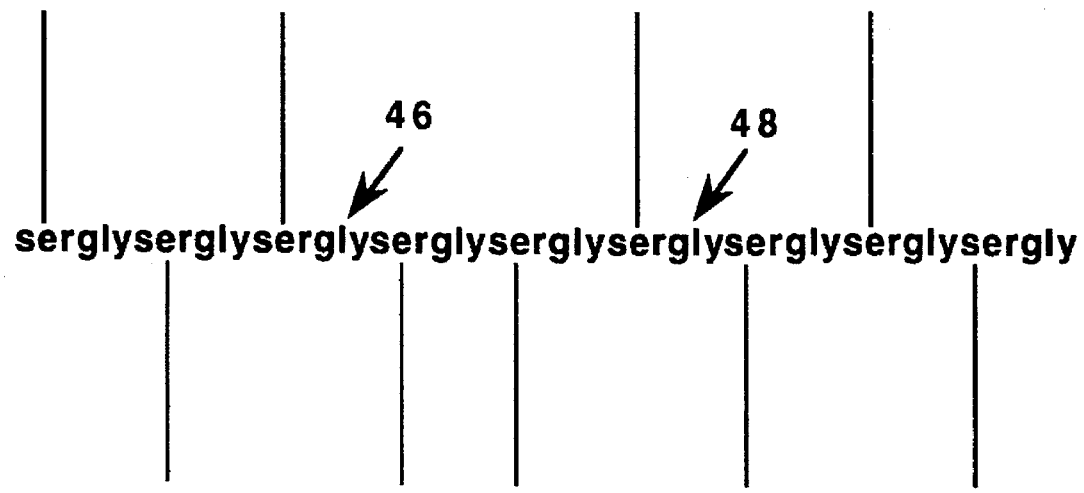
Figure 12B:
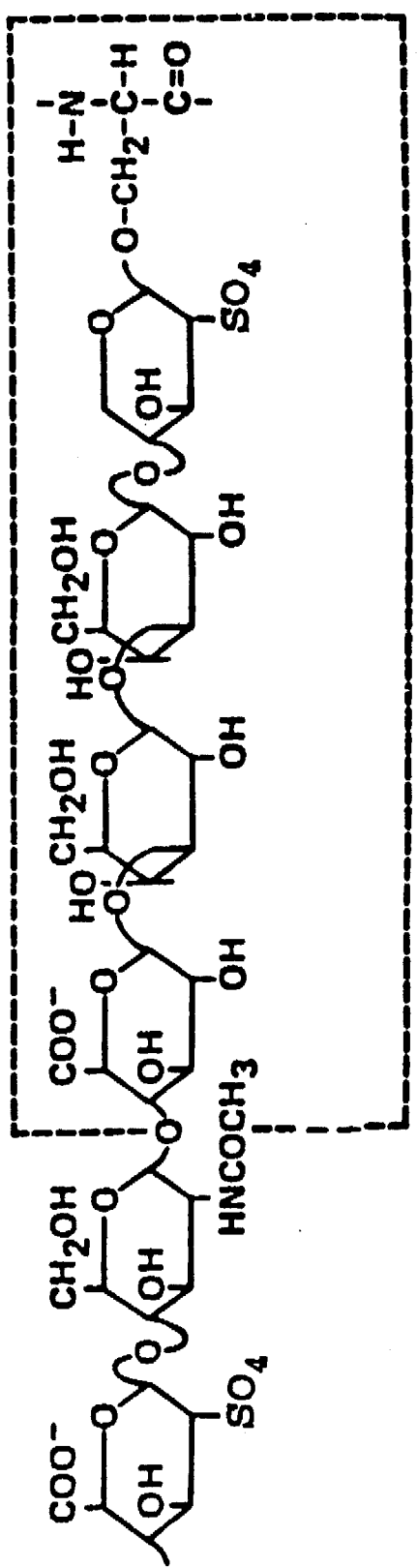
Figure 13:
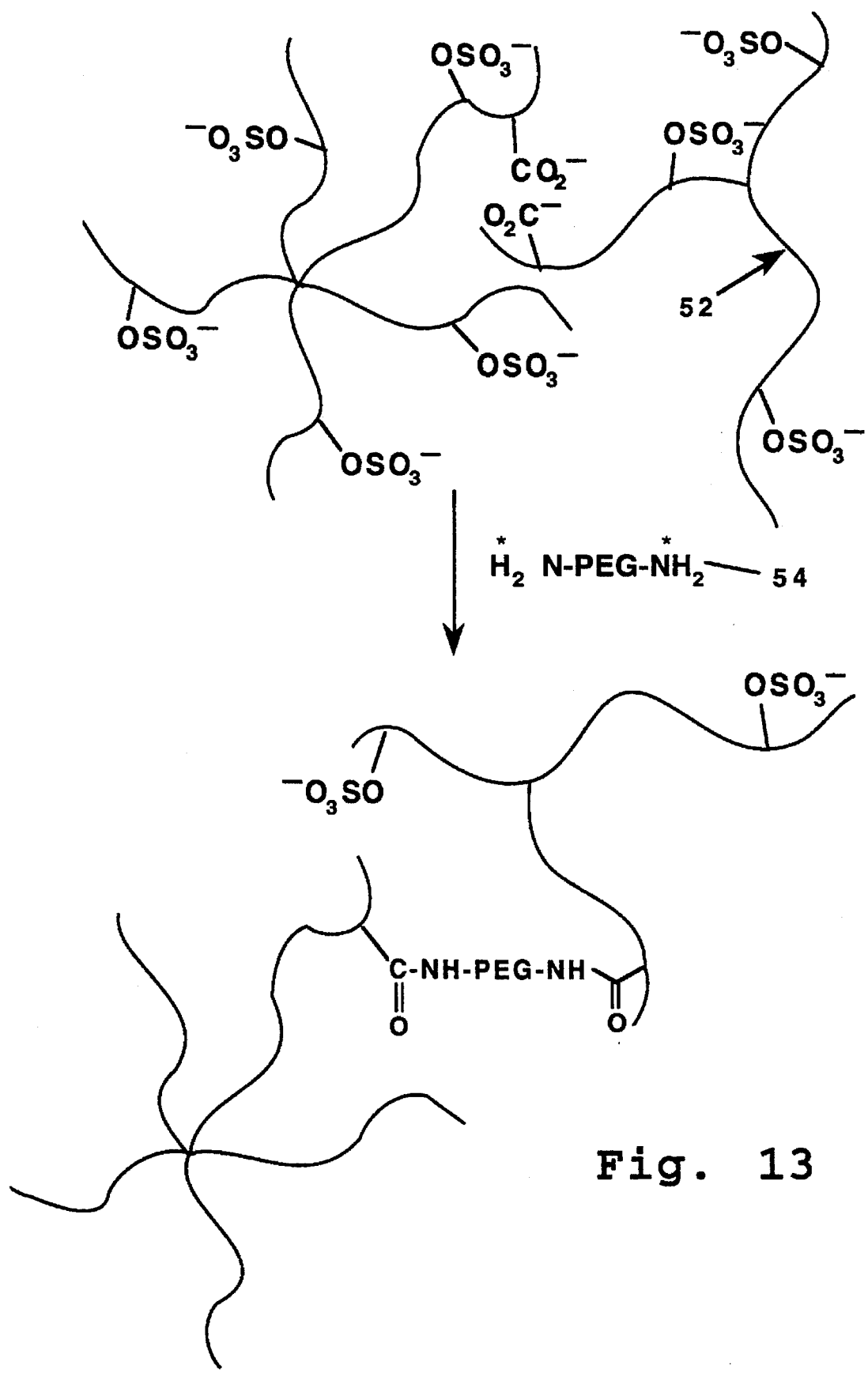
Figure 15A:
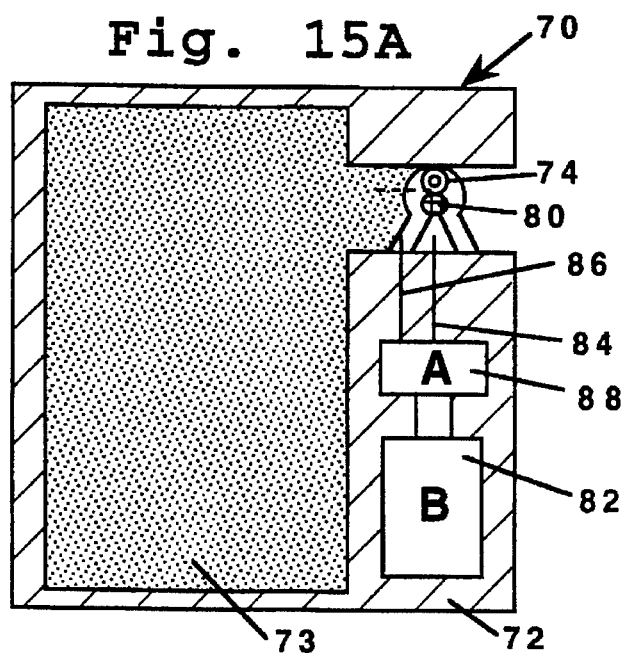
Figure 15B:
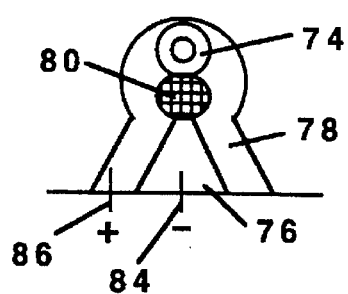
Figure 15C:
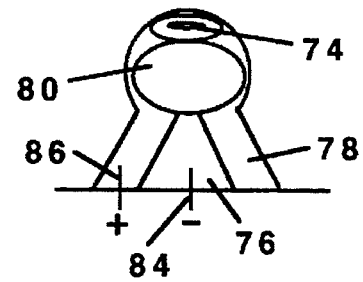
Figure 16:
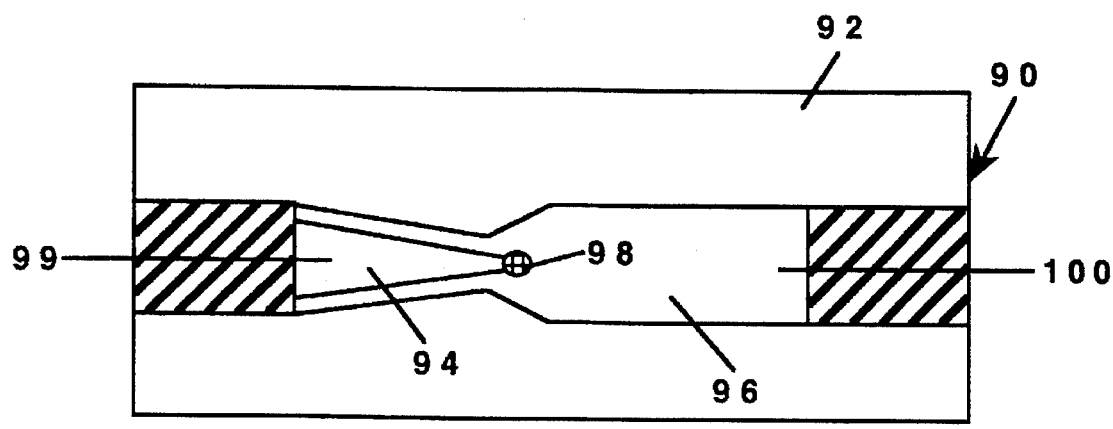
Figure 17:
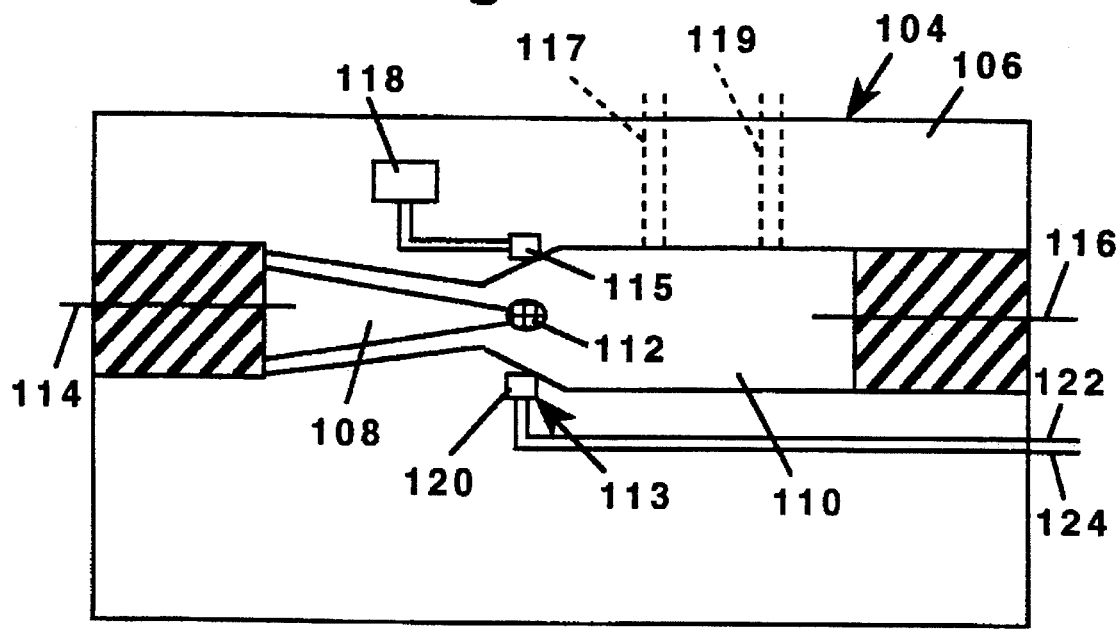
Figure 18A:
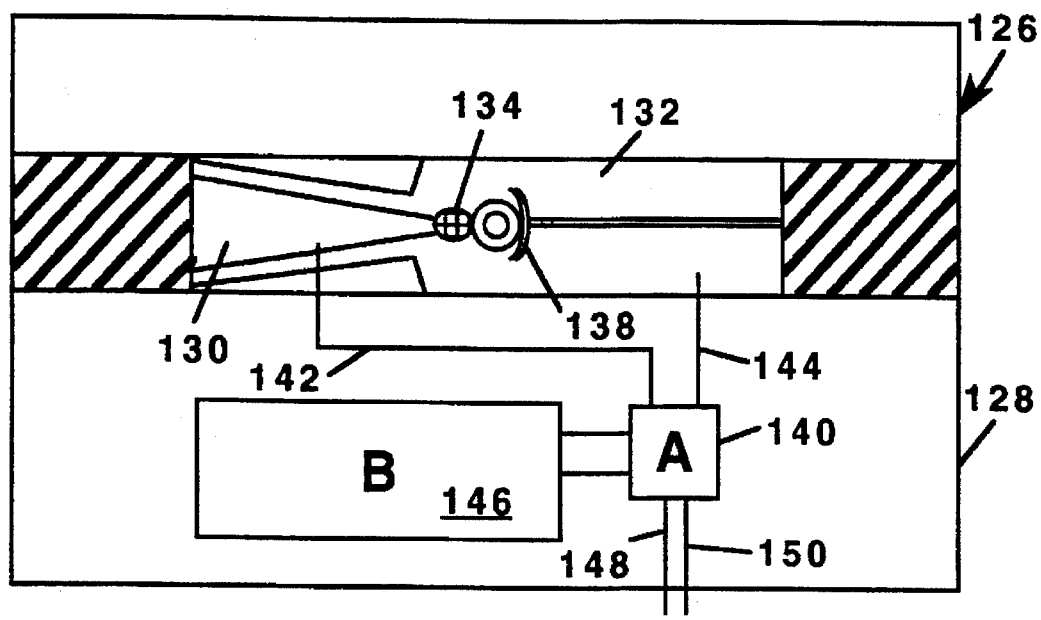
Figure 18B:
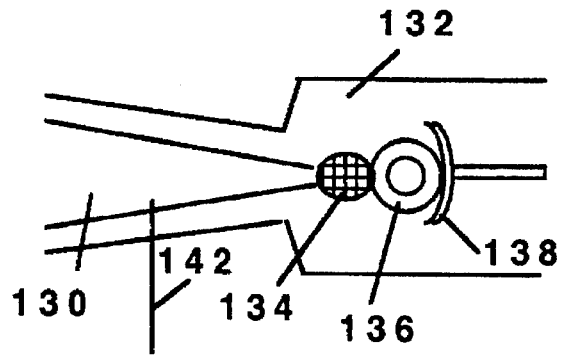
Figure 18C:
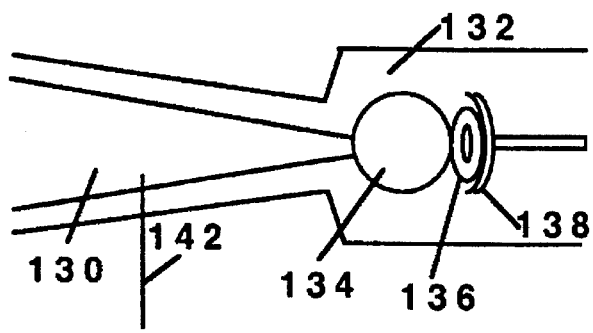
Figure 19:
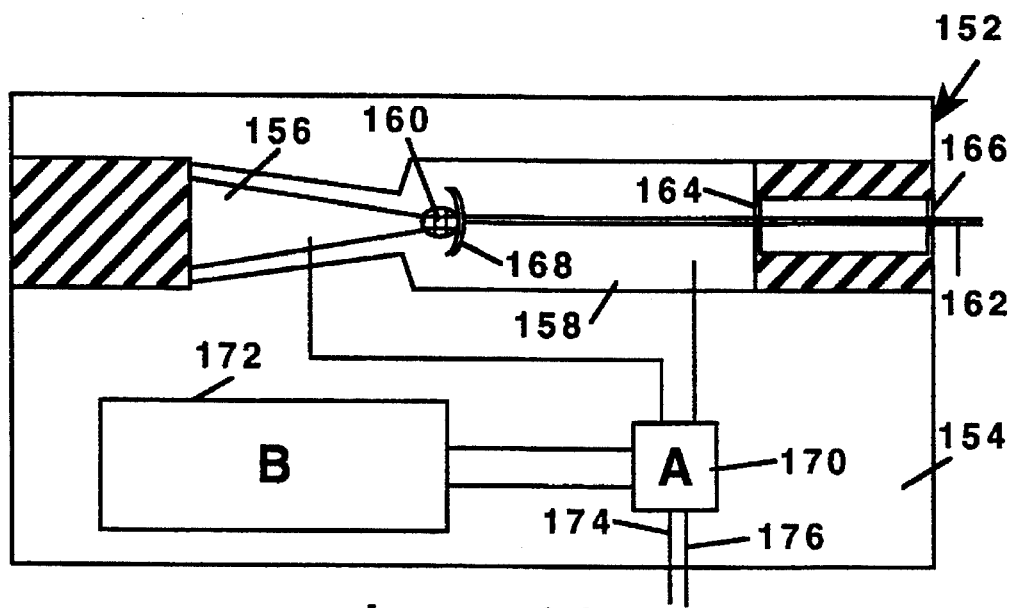

4A), showing the accumulation of charge carriers at the diode interface in the direction of current flow (FIG. 4B), and the depletion of charge carriers at the diode interface in the direction of high diode resistance (FIG. 4C);

FIGS. 5A–5D are photographs illustrating the voltage-dependent changes of the physical properties of the polymer-matrix microparticle in FIG. 1;

FIG. 6 shows the time course in the swelling of the microparticle in FIG. 1 in response to a voltage of +3 V (open squares) and –2.5 V (closed squares);

FIG. 7 is a plot showing the degree of voltage dependence of microparticle swelling in the microparticle in FIG. 1;

FIGS. 8A and 8B shows the voltages applied to the microparticle in FIG. 1 (8A) and the corresponding instantaneous currents measured across the microparticle (8B);

FIG. 9 is a least-squares fit of the instantaneous current-voltage data from FIG. 8B;

FIG. 10 shows the time course of the force generated by a polymer-matrix microparticle that has swollen in response to a voltage pulse of –8 V, where a control voltage pulse of +8 V is also shown;

FIG. 11 shows a generalized structure of a sulfated comb-polymer glycoprotein used in forming a polymer-matrix microparticle in accordance with the invention;

FIGS. 12A and 12B show the backbone structure of a heparin sulfate proteoglycan polymer (FIG. 12A), and the side chain structure of the same polymer (FIG. 12B);

FIG. 13 shows a crosslinking reaction used in forming a crosslinked polymer matrix for use in the invention;

FIGS. 14A–14D illustrate steps in forming polymer-matrix microparticles by lipid encapsulation;

FIGS. 15A–15C show in cross sectional views, a miniature drug-delivery device constructed in accordance with the invention (FIG. 15A), where the polymer-matrix microparticle particle in the apparatus is shown in a condensed "open-valve" condition (FIGS. 15A and 15B) and in a decondensed "close-valve" condition (FIG. 15C);

FIG. 16 shows in cross sectional views, a diode device constructed in accordance with the invention;

FIG. 17 shows in cross sectional view, a optical sensing device constructed in accordance with the invention;

FIGS. 18A–18C show in cross sectional views, a miniature pump device constructed in accordance with the invention (FIG. 18A), where a polymer-matrix microparticle in the device is shown in a condensed "chamber-filling" condition (FIGS. 18A and 18B) and a decondensed "pumping" condition (18C); and FIG. 19 shows in cross sectional view, a miniature mechanical actuator device constructed in accordance with the invention, where a polymer-matrix particle in the device is shown in a condensed "relaxed" condition.

DETAILED DESCRIPTION OF THE INVENTION

I. Definitions

As used herein, the terms below have the following definitions unless indicated otherwise.

"Polyionic polymers" or "polyionic polymer filaments" are polymers containing multiple charged subunits (subunits containing at least 1 negative or positive charge at a pH between about 4–10), and having a net negative (polyanionic) or net positive (polycationic) charge.

"Polyanionic polymers" or "polyanionic polymer filaments" are polyionic polymers in which the charged subunits are ionizable, negatively charged subunits, typically sulfate, sulfonate, or carboxylate, or phosphate groups. Such polyanionic polymers or polymers filaments are also referred to herein as "sulfated, sulfonated, carboxylated, or phosphated" polymers or polymer filaments, respectively.

"Polycationic polymers" or "polycationic polymer filaments" are polyionic polymers in which the charged subunits are ionizable positively charged subunits, typically primary, secondary, tertiary amine groups or in which the charged subunits contain quaternary amine groups.

"Polyionic hydrophilic polymers" are polyionic polymers which are soluble in an aqueous solution, at a selected pH between 4–10, preferably having a partition coefficient, expressed as log n-octanol/water, normalized to 0 for H, of less than zero.

"Comb polymers" or "comb-polymer filaments" are polymer filaments composed of a polymeric backbone chain and a plurality of polymer side chains attached to the backbone polymer at spaced positions along the backbone chain, and radiating outwardly from the backbone chain.

A "comb-polymer glycoprotein" refers to a comb polymer having a polypeptide backbone chain to which is attached, at spaced positions along the polypeptide chain, a plurality of anionic polysaccharide side chains.

A "sulfonated, sulfonated, carboxylated, or phosphated comb-polymer glycoprotein" refers to a polyanionic comb-polymer glycoprotein in which the polysaccharide side chains carry sulfate, sulfonyl, carboxyl, or phosphate groups, respectively, at one or more sugar residues.

"Glycosaminoglycans" consist of disaccharide repeating units containing a derivative of an amino sugar (glucosamine or galactosamine) where at least one of the sugars in the disaccharide contains a carboxylate or sulfate group. Exemplary glycosaminoglycans include hyaluronate, chondroitin sulfate, keratin sulfate, heparin sulfate and heparin.

"Proteoglycan" refers to a polypeptide backbone to which is attached multiple anionic heteropolysaccharide sidechains which are generally glycosaminoglycans. Proteoglycans may form aggregates around other biopolymers, such as a polysaccharide molecule.

A "crosslinked polymer matrix" is a matrix of polymer filaments in which the filaments are crosslinked by covalent crosslinking between and/or among filaments by bifunctional or polyfunctional crosslinking agents, or crosslinked by ionic bonds between anionic groups on the polymer filaments and multivalent cationic crosslinking species;

A "multivalent solute species" is a divalent or multivalent anionic or cationic solute species.

"Microparticles" refer to particles which are formed of a crosslinked polyionic polymer matrix, and which have condensed-state sizes in the range between about 0.05 to 50 μm (μmeter), preferably 0.05 to 5 μm (μmeter).

II. Polymer-Matrix Microparticles

This section describes the preparation and properties of polymer-matrix microparticles used in various aspects of the invention.

The microparticles are composed of crosslinked polyionic filaments, and preferably a crosslinked network of polyanionic filaments, such as sulfated, sulfonated, carboxylated or phosphated polymers, such as comb-polymer glycoproteins. Exemplary polymer filaments, and methods of preparing the crosslinked matrices, either by isolation from biological sources, or by synthetic means, will be described below.

According to one aspect of the invention, the particles can be cycled rapidly between condensed and decondensed states, by subjecting the microparticles to an asymmetric electric field. A voltage potential in one direction produces swelling, and in the opposite direction, condensation (partial or complete condensation). In the condensed state, the microparticles are relatively dense and opaque, and have preferred sizes in the size range between 0.05 and 5 µm (micrometer). In the decondensed state, the polymer matrix expands, typically 2–3 fold in volume and becomes more transparent.

According to another aspect of the invention, the microparticles have the ability to be function as diodes, either in a condensed or partially decondensed state, when placed in an asymmetric field configuration.

A. Diode Properties

FIG. 1 shows a diode switching device 10 constructed according to one embodiment of the invention, and designed for measuring changes in the current flow when an electric field is applied across a microparticle 12. A microparticle in accordance with the invention is shown partially drawn into the tip of a glass micropipette 14, such that a first or interior region 36 of the particle surface is in contact with an interior aqueous electrolyte solution 16 inside of the pipette. A second or exterior region 38 of the particle surface is in contact with an exterior aqueous electrolyte solution 20 contained in a vessel 22.

A voltage potential across the microparticle is established by electrodes 24, 26 in contact with the interior and exterior electrolyte solutions, respectively. The pipette potential is controlled by a current-to-voltage converter in connection with a unity-gain differential amplifier, both indicated schematically at 28. An interface 30 is used to apply the voltage and sample the current at selected intervals, e.g., 2.5 msec. The diode arrangement is described in Example 2.

Figure 2A:
FIGS. 2A and 2B show a series of positive and negative voltage levels (FIG. 2A) and the corresponding currents (FIG. 2B) produced across the microparticle in FIG. 1.
Figure 2B:
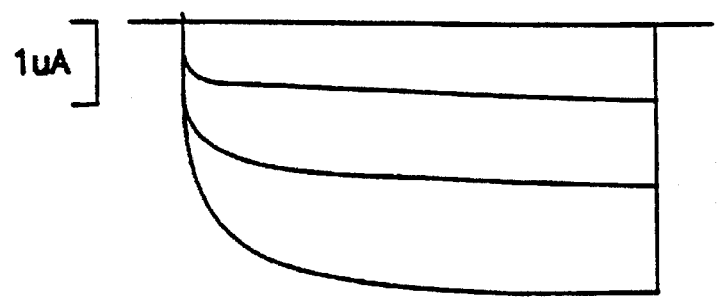

FIGS. 2A and 2B show voltage and time dependence of currents measured through mast cell-derived biopolymer particles in response to different voltage potentials. As used herein, a "–" or negative voltage means that the voltage applied to the interior of the pipette is negative with respect to the voltage applied to the exterior solution in vessel 22. Similarly, a "+" or positive voltage means that the voltage applied to the interior of the pipette is positive with respect to the voltage applied to the exterior solution in vessel 22.

In FIG. 2A is shown the voltage potentials ranging from −5 V to +5 V to which the particle was subjected. The corresponding currents induced across the microparticle are shown in FIG. 2B. The upper trace of FIG. 2B, indicating zero current, represents the current measurements made at zero or positive potential across the particles. The three lower traces correspond the currents measured at the three negative potentials applied.

As seen in FIG. 2B, application of a negative voltage across the microparticles results in a near-instantaneous ($\leq$2.5 msec) inward current. The instantaneous current is followed by a slower exponential current having a time constant of about 88 msec.

Figure 3:
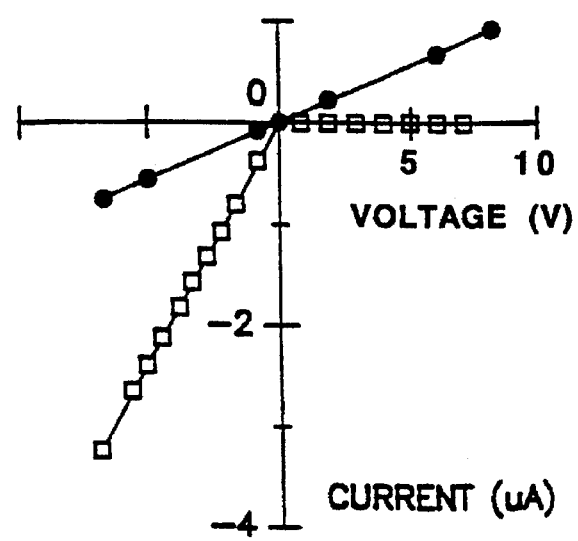
FIG. 3 is a plot of the steady-state current versus applied voltage for the microparticle in FIG. 1 (open squares) and for the pipette in FIG. 1 alone, i.e., in the absence of microparticle.

FIG. 3 shows a plot of current measured as a function of voltage applied to the particle. The closed circles show that the current of the testing apparatus pipette in the absence of a particle is linear and ohmic at all voltages. It can be seen that there is a strong rectification of the current through the particle matrix at zero voltages. At negative voltages, current flow was proportional to voltage applied.

As observed from the data of FIG. 3, the particle functions as a diode having a conductance that is 100-fold larger at negative potentials than at positive potentials. In a series of 5 experiments, particle conductance changed from about 5 nS (nanoSiemans or $10^{-9}/\Omega$) at positive potentials to about 500 nS at negative potentials. These values were uncorrected for leakage current, which may account for the current at positive voltages. At negative voltages, the conductance of the pipette with a particle in its tip was up to 6 times higher than the pipette alone. Similar diode characteristics were obtained for a diode containing a synthetic microparticle such as described below.

As can be appreciated from FIG. 1, the diode configuration is designed to produce an asymmetrical electrical field when a voltage potential is placed across the microparticle. The relationship between asymmetrical field lines and the diode behavior of microparticle can be understood with reference to FIGS. 4A–4C.

These figures show, from FIG. 1, pipette 14 defining an interior chamber 32 containing an aqueous electrolyte solution, a microparticle 12 placed against the end of the pipette, and a second electrolyte solution 20 in an exterior chamber 34 defined by vessel 22.

According to an important feature of the diode configuration, the concentration of field lines, such as lines 33, shown in FIGS. 4A–4C seen by the interior surface region of the microparticle (indicated at 36) in contact with the electrolyte solution within the pipette is substantially greater than that seen by the exterior surface region (indicated at 38) in contact with the exterior solution. As will be discussed below with reference to FIGS. 4B and 4C, the higher concentration of field lines at the interior surface region acts to populate charge carriers at this surface region, when the voltage across the microparticle has one polarity, and to deplete charge carriers at this region when the voltage across the microparticle has the opposite polarity.

The asymmetric field lines may be produced, according to one embodiment, by a configuration such as shown in FIG. 4A, in which the solid angle $\alpha$ subtending interior surface region of the particle is substantially less than the solid angle $\beta$ subtending the exterior surface region of the particle. In FIG. 4A, a solid angle $\alpha$ subtending the pipette's interior side, and the remainder angle $\beta$ subtending the pipette's exterior side, are taken with reference to the center of the microparticle, as indicated.

Also as seen in this figure, the interior surface region of the microparticle in contact with the electrolyte in the first chamber, which is defined by solid angle $\alpha$, is substantially less than microparticle's exterior surface region that is in contact with the electrolyte in the second chamber, defined by remainder angle $\beta$. Preferably the exterior surface region of the microparticle (which is proportional to the subtending solid angle in a spherical particle) is greater than the interior surface region by a factor of at least 25–100.

In the configuration shown in FIG. 4B, the microparticle is formed of a negatively charged polymer matrix, and a negative voltage is applied across the particle. The higher voltage drop at the interior surface region interface (due to the smaller area of the interior surface region) relative to that across the exterior surface region creates a higher localized concentration of electrolyte anions, and a corresponding concentration of positive counterions, at the inner surface interface. This has the effect of populating the junction between the electrolyte and microparticle with charge carriers, creating a low-resistance interface that favors current flow in the direction of the applied voltage.

In the configuration shown in FIG. 4C, a positive voltage has been applied across the same microparticle. As shown, the positive interior voltage acts to draw electrolyte anions (and charge-balancing cations) away from the interior interface. Because the microparticle, indicated at 12', is negatively charged, ion depletion at the diode junction cannot be readily replaced by anion flow through the matrix, with the result that the interior interface, indicated at 36', is depleted of charge carriers, resulting in a high-resistance barrier to current flow. The greater exterior surface portion of the microparticle is indicated at 38'.

Where the microparticle is composed of a positively charged polymer matrix, the microparticle will operate as a diode with the opposite voltage polarity. Here a negative voltage will deplete the interface charge carriers, effectively blocking current flow, while a positive voltage will densely populate the interface, promoting current flow.

B. Particle-Decondensation Properties

Another feature of the microparticles employed in the invention is the ability to undergo rapid condensation/decondensation cycles in response various stimuli, including current flow through the microparticle and displacement of multivalent ions in the matrix. The present section will examine the changes in condensation state due to current flow.

In experiments carried out in support of the invention, cross-sectional areas of microparticles derived from beige mouse cell microparticles were measured from images according to the methods detailed in Example 3. The particles were stimulated by application of voltage in the pipette configuration shown in FIG. 1. Relative swelling was calculated relative to the cross-sectional area of the particle prior to application of voltage.

The microparticle comprising the granule matrix was subjected to voltage potentials ranging from −5 V to +3 V. At each voltage, measurements of size and conductivity were made, and opacity was recorded, as described below.

FIGS. 5A–5D show Nomarski optics photographs of a microparticle undergoing decondensation with application of a negative voltage across the microparticles, according to the methods detailed in Example 2 and depicted in FIG. 1. As can be seen in the two top photos (+3 V and 0 V), when subjected to positive or zero voltages the particle was condensed and refractile relative to the surrounding medium. In contrast, at negative potentials, the particle was swollen and transparent. In general, biopolymer matrix particles formed from mast cell granule matrix are refractile or opaque in their condensed state and transparent in their expanded or de-condensed state.

FIG. 6 shows relative swelling over time of a microparticle subjected to a +3 V potential (open squares) and to a −2.5 V potential (open circles), where the voltage pulses were initiated at time 0 and terminated 1 second later. As seen, the microparticle swelled to half its final expanded size within about 1/30 sec (1 video frame) of application of the −2.5 V potential, corresponding to a swelling time constant (half response time) of about 33 msec. The instantaneous swelling was followed by a slower exponential phase having a time constant of 212 msec. Relative final size was about two times the size of the condensed particle in the experiment shown.

In a similar experiment, in which swelling was analyzed during application of a 1 V negative potential across a particle, a time constant of swelling of 422 msec was measured. Upon discontinuance of the negative voltage potential across the particle, the microparticle exposed to −2.5 V contracted to its original size within 300 msec, as seen in FIG. 6.

FIG. 7 shows a plot of relative swelling of a polymer-matrix microparticle as a function of applied voltage. The data show that the particle size increases linearly as a function of negative potential. No significant swelling occurred at zero potential or at positive voltage potentials.

A series of experiments in which a particle was initially held in a decondensed state at −8 V, then was exposed a more positive voltage potential, ranging from −2.5 V to about +7 V was carried out, employing the voltage protocol indicated in FIG. 8A. Instantaneous current was measured 2.5 msec after voltage change, to determine instantaneous conductance prior to significant recondensation of the particle matrix (FIG. 8B).

In contrast to the steady state conductance of this particle at negative potentials (510 nS), an instantaneous conductance of 390 msec was observed. Mean instantaneous and steady state conductances measured over four separate experiments were 352 nS and 470 nS, respectively. A plot of instantaneous current vs. voltage potential applied is shown as FIG. 9. Here, it can be seen that the current is roughly proportional to the voltage applied.

The results are consistent with the diode-junction model discussed in relation to FIGS. 4A–4C. In particular, the model predicts that with a high population of charge carriers at the microparticle junction, a transitory voltage-dependent current can be induced in the direction opposite normal current flow, as the population of charge carriers at the junction are depleted.

Depending on the cation composition of the medium, the microparticle may condense completely or only partially on voltage reversal. The change in condensation state of the particle after voltage reversal may contribute to diminution of current through the microparticle, or may be a result of reduced ion flow through the particle.

As just indicated, the microparticle diode effect has also been observed with decondensed microparticles, e.g., particles in a electrolyte solution lacking divalent cations needed for condensation. Here the application of voltage in the direction supporting current flow is effective to produce additional decondensation (swelling) of the microparticle, but application of voltage in the opposite direction is effective to block current flow, even though the microparticle is still in a substantially decondensed, though somewhat shrunken state.

The decondensation of microparticles, in response to voltage changes, as described above, can be converted to mechanical work as illustrated in FIG. 10. A miniature stress transducer was used to measure the force exerted by the particle as it was induced to expand from condensed form to a decondensed form, as detailed in Example 4. Briefly, a microparticle was placed in close proximity to a stress-transducing beam, and exposed to a potential of −8 V. Expansion of the particle caused bending of the beam. An average force of 131 µg was generated by single particles (n=5). Assuming that 1 µm$^2$ of granule is in contact with the stress transducer, this force translates to a pressure of approximately 12 bar.

The application of the particle condensation-decondensation and/or diode properties, when the microparticle is exposed to an asymmetric electric field, will be described in Section III below.

B. Isolation of Microparticles

Microparticles suitable for use in the methods and compositions of the invention may be isolated from one or more suitable biological sources, including cultured cells, as described below. In certain embodiments of the invention, microparticles are isolated as the intact cores of secretory granules. Such granules are typically composed of a membrane surrounding a core of highly charged biopolymers. Proteoglycans, as found in mast cell granules, are particularly preferred for forming polymer-matrix microparticles for use in various embodiments of the invention described herein. Glycoproteins, such as form mucous, may also be useful in forming microparticles for certain applications.

Secretory granules can be obtained from mast cells, goblet cells, chromaffin cells and other secretory cells, according to the particular biopolymer and chemical properties required. For example, goblet cell granules contain mucin, a mixture of linear polyanionic glycoproteins, whereas mast cell granules contain heparin proteoglycans, which contain ester sulfate groups. Biopolymers isolated from each of these sources have different characteristics. Mucin-containing granules decondense to form a diffuse gel, while mast cell-derived heparin proteoglycan particles maintain a particulate form following decondensation. Other secretory granule derived materials include, but are not limited to, chromogranin A from chromaffin granules of the adrenal medulla and acidic protein SP-1 from parathyroid granules. In addition, polyanionic chromogranin A-like matrices are present in secretory cells of the thyroid, pancreatic islet cells, sympathetic ganglia, anterior pituitary and gastric antrum.

Preferred isolation techniques for secretory granules from cells include homogenizing the cells with a mechanical homogenizer, treating the cells with detergents, rupturing the cells by sonication, or combinations thereof. The homogenizing or sonicating conditions may leave the granule membranes substantially intact on the granules. Alternatively, cells may be stimulated to release the secretory granules, such as by contact with a releasing agent. Preferably, to form biological microparticles used in the inventions described herein, membranes will be removed, either during the isolation process, or by detergent means thereafter, as described for mast cell granules in Example 1. After the secretory granules are released from the ruptured cells, the granules are then separated from the cell debris by centrifugation in a density gradient, for example, a sucrose gradient or a metrizamide gradient. Such cell rupturing and centrifugation procedures are well known in the art.

Preferred secretory granules for isolation of polymer-matrix microparticles include mast cell granules. Mast cells can be obtained from the peritoneal cavity of various rodent species. Adult beige mice (bgj/bj, Jackson Laboratories, Bar Harbor, Me.) are particularly convenient sources of such cells, as described in Example 1. Cells are collected by peritoneal lavage, and the isolated cells are equilibrated in an isosmotic "extracellular" solution. Cells are stimulated to secrete granules, by use of a secretagogue, such as compound 48/80, or by mild sonication, as detailed in Example 1.

These alternative methods of stimulating release of granules from secretory cells result in differences in initial appearance of the granules. Granules released by stimulation with Compound 48/80 decondense rapidly upon release, but can be recondensed to within 5% of original intracellular volume by immersion, for example in a solution containing 50 mM histamine, pH 3. Granules isolated by mild sonication retain an intact granule membrane and their condensed form. Membranes enclosing the granules may then be removed by conventional techniques such as detergent treatment (e.g., Tritonx 100) or strong sonication.

Mucin containing secretory granules may be isolated from secretory cells located in the respiratory system called "Goblet" cells. When released from the granules, mucins undergo massive swelling to form a gel in aqueous solution. (Verdugo) Mucin particles can be isolated from primary cultures of Goblet cells from rabbit trachea, according to standard methods. Such cultured cells spontaneously degranulate in a manner similar to mast cells. Upon release from the cell, mucin-containing granules swell rapidly for 5–10 sec. The granules generally anneal with each other in the extracellular fluid. The swelling process can be retarded significantly by elevation of calcium content in the extracellular medium (Verdugo).

C. Synthetic Microparticles

Polymer-matrix microparticles having the diode and rapid condensation/decondensation properties described above can also be made synthetically by a variety of methods. The microparticles are made by forming cross-linking polyionic hydrophilic polymers under conditions which lead to cross-linked matrices in the 0.05 to 50 µm, preferably 0.05 to 5 µm particle-size range, when the particles are in their condensed states.

A. Filament Preparation and Crosslinking

Below are described two general methods for producing polyionic filament components in the microparticles.

1. Prepolymerized ionic polymer filaments.

In one embodiment, the microparticles are prepared by crosslinking existing ionic polymer filaments. Polymer filaments that are suitable include sulfated, sulfonated, carboxylated, or phosphated hydrophilic polymers, in forming negatively charged polymer matrices, and amine-containing hydrophilic polymers, in forming positively charged polymer matrices.

Preferred polyanionic polymer filaments include sulfated proteoglycans, e.g., sulfated heparin, and other sulfated polysaccharides, such as sulfated cellulose or cellulose derivatives, carrageenin and dextran sulfate, mucin, sulfated polypeptides, such as polylysine with sulfated amine groups, and glycopeptides with sulfonate-derivatized saccharide or peptide subunits, and hyaluronic acid.

One type of preferred polyanionic polymer filament includes sulfated, sulfonated, carboxylated, or phosphated comb-polymer glycoproteins. The basic structure or this type of polymer is shown in FIG. 11. The polymer, indicated at 40, generally includes a polymeric backbone 42, such as a polypeptide, such as one having repeating subunits, such as repeating amino acid subunits. Attached to the backbone, at attachment points spaced along the backbone, are a plurality of polysaccharide side chains, such as side chains 44. The side chains carry negatively charged sulfate groups, as shown, typically several per chain, but an average of at least about 1 negatively charged group per chain.

Where the backbone polymer contains amino acid residues, the subunit side chains may have a variety of selected chemically reactive groups, such as a hydroxyl, carboxy, or amino groups, by which the side chains of the comb-polymer can be attached to the polymer, such as illustrated for the SER-GLY repeat backbone shown in FIG. 12A.

If the comb-polymer can be prepared de novo, a variety of coupling reaction are available for attaching the side chains covalently to the backbone polymer. In general, this is done by activating one end of the polysaccharide side chains, and reacting the activated chains with a backbone under conditions effective to couple the activated chains to corresponding reactive side-chain groups on the polypeptide or other polymer backbone. Coupling reactions suitable for coupling to carboxy, hydroxyl, amino, or sulfhydryl groups are well known.

The percentage of backbone reactive groups, and the relative lengths and stoichiometry of the polymer filament backbone chain and side chains is preferably such that the comb-polymer preferably includes at least about 80-95% by weight polysaccharide components.

One preferred sulfated comb-polymer glycoprotein is heparin sulfate proteoglycan, whose structure is indicated in FIG. 12A. As seen, the polymer (indicated at 46) has a polypeptide backbone 48 composed of repeating SER-GLY dipeptide subunits, with heparin chains, indicated by vertical lines, attached to the backbone at some of the SER residues, through the SER hydroxyl group. A portion of a heparin side chain is shown in FIG. 12B.

Proteoglycan polymer filaments of this type may be synthesized following known methods, such as those outlined above. Alternatively, some proteoglycan filaments, such as heparin sulfate proteoglycan, can be obtained by isolation from biological sources.

The preformed filaments may be crosslinked by bifunctional or multifunctional crosslinking agents effective to form intermolecular links between the filaments. In one general embodiment, the crosslinking agent may be long, hydrophilic polymer chain, such as a polyethyleneglycol (PEG) chain, having activated end groups effective to form covalent linkages to selected reactive groups on the polysaccharide side chains of the polymer filaments.

FIG. 13 illustrates one exemplary crosslinking reaction in which carboxyl groups in sulfated heparin side chains, such as shown at top in the figure, are linked by an activated diamino-PEG molecule, as indicated. Methods for activating crosslinking agents of this type, and for crosslinking polymer filaments by the activated agents, are well known (Wong, Antonietti, Huang, Funke). Alternatively, the carboxyl groups may be activated, for reaction with free amine groups in the crosslinking polymer.

The crosslinking reaction is preferably one which can be initiated by heat, e.g., by raising the temperature of the reaction by infrared irradiation, or by radiation, such as visible light, UV or X-irradiation, according to known polymer forming reactions.

2. Polymer synthesis

In another general embodiment, the charged polymer filaments are formed de novo in a polymerization and crosslinking reaction. A variety of monomer systems for forming crosslinked microparticles have been proposed, for example vinylpyridine, 2-hydroxyethyl methacrylate, acrylamide, dimethylacrylamide, acrolein, poly(N-isopropyl)acrylamide, amino acid monomers, saccharide monomers, alkylcyanoacrylates, glycidyl methacrylate, and hyaluronic acid (e.g., Wu, Arshady, Margel, Okubo, 1992a, 1992b, Kreuter, Kamei, Fujimoto, Yui, and Hosaka).

These monomers are mixed with selected charged-group monomers, such as methacrylic acid, vinyl monomers having carboxyl or amine groups (Arshady) or monomers in which the reactive group has been converted to a sulfate, sulfonate, or phosphate group, by standard reaction methods. Typically, the charged monomer will be included in a range from about 5-50 mole percent of uncharged monomer, although the polymer may be formed entirely from charged monomer units.

The polymerized chains may be crosslinked by free radical polymerization, by inclusion of crosslinking monomers, such as methylene-bis-acrylamide or divinylbenzene (e.g., Okubo, Arshady, Kreuter), or by crosslinking through polymer chains, as above.

In both of the approaches discussed above, the polymer filaments may be modified, before or after crosslinking to form microparticles, to introduce charged groups, and/or binding groups on the filaments. Thus, the initial microparticle may be formed of substantially uncharged filaments as long as the filaments contain groups that can be modified to form the desired charged group.

Similarly, the charged groups can be introduced by forming the microparticle to include a ligand-specific binding agent, such as lectin, and introducing the complement of the binding agent, e.g., sulfated heparin, into the matrix after particle formation (Tanaka).

The polymer filaments can be constructed and/or modified after particle formation to achieve desired characteristics. For example, when the polymer matrix is to be condensed or decondensed within a desired pH range, the polymer is prepared to include the charged group, e.g., carboxyl group or amine group, whose $pK_a$ is within such pH range.

Similarly, where the polymer matrix is to be used in delivering selected biological or chemical ligand species, preferably charged species, the microparticle is formed to include binding molecules capable of binding the ligand specifically and with high affinity.

B. Microparticle Formation

Several methods are available for forming microparticles having desired sizes in the size range 0.05 and 50 μm, preferably 0.05 to 0.5 μm. These include:

1. Emulsion Polymerization

In this method, monomers are dissolved in a continuous aqueous phase also containing emulsifier micelles plus excess free monomer stored in large droplets in suspension. Polymerization reactions, such as by addition of an initiator molecule or high-energy radiation, leads to polymerization in the regions of the micelles. Phase separation and formation of solid particles can occur before or after termination of the polymerization reaction. Particle size can be controlled by monomer density, micelle density, and polymerization conditions (Kreuter, Cadan, Vanderhoff). As with several of the published methods cited herein for microparticle preparation, it will be appreciated that the published method may need to be modified to include a desired percentage of charged monomers, as discussed above.

2. Emulsion Polymerization in Continuous Organic Phase

In this method, water-soluble monomers are added to a water-in-oil emulsion stabilized by a surfactant, under conditions that polymerization is initiated in the aqueous phase droplets (Kreuter).

3. Precipitation Polymerization

Precipitation polymerization involves polymerization starting from a monomer solution in which the polymer (or microparticle) is insoluble (Kawaguchi, 1991, 1992, 1993, Pelton, 1986, 1988, Tai). Typically in this method, polymerization of monomers in solution is allowed to proceed until desired size polymer filaments are formed, usually under conditions of vigorous mixing.

This method (following Kawaguchi) was followed in preparing synthetic microparticles described in several particle-condensation studies conducted in support of the invention, where the crosslinked polymers described in the reference were prepared to include carboxylated subunits. The polymer mixture included methacrylic acid (10 mmol) /nitrophenyl acrylate (10 mmol)/methylene bis acrylamide (5 mmol)/ethanol (35 g), employing 0.75 g initiator AIBN. The reaction was carried out at 60° C. for 22 hours under nitrogen. The particle may be treated by reaction with ethylene diamine 100 eq/1 eq particle at room temperature for 48 hours.

4. Encapsulated polymer method

In this method, a polyanionic, hydrophilic polymer is crosslinked in an encapsulated form, followed by removal of the encapsulating membrane to leave cross-linked, decondensed particles of a desired final size. The method is illustrated in FIGS. 14A–14D for the preparation of particles using encapsulating liposome membranes.

Figure 14A:
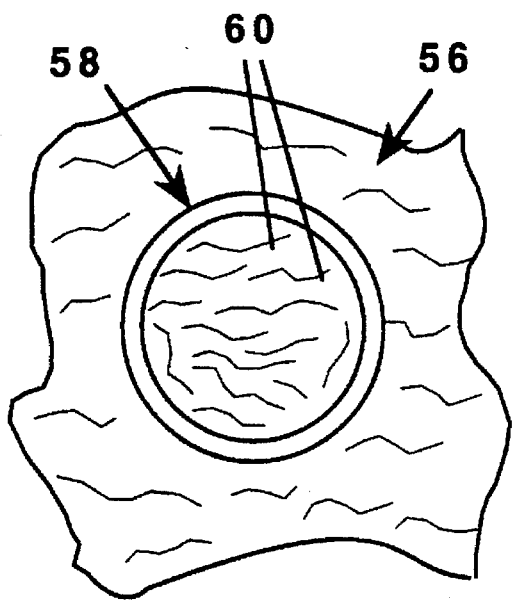

Initially, and with reference to FIG. 14A, an aqueous solution or suspension of the polymer and cross-linking agent (aqueous polymer medium) is encapsulated in lipid bilayer vesicles. A variety of vesicle-forming methods, such as lipid hydration, reverse-phase evaporation, solvent injection, and freeze-thaw methods are available for encapsulating aqueous material in lipid vesicles.

In a preferred method, the aqueous polymer medium is used to hydrate a dried lipid film formed of vesicle-forming lipids, such as a mixture of phosphatidylcholine (lecithin) and cholesterol. The hydration is carried out under mild agitation, to form liposomes with heterogeneous sizes between about 0.05 and 20 microns. The suspension, indicated at 56 in FIG. 14A, contains liposomes, such as liposome 58 with encapsulated polymers, such as polymers 60, as well as polymers in the bulk phase of the suspension, as shown.

Figure 14B:
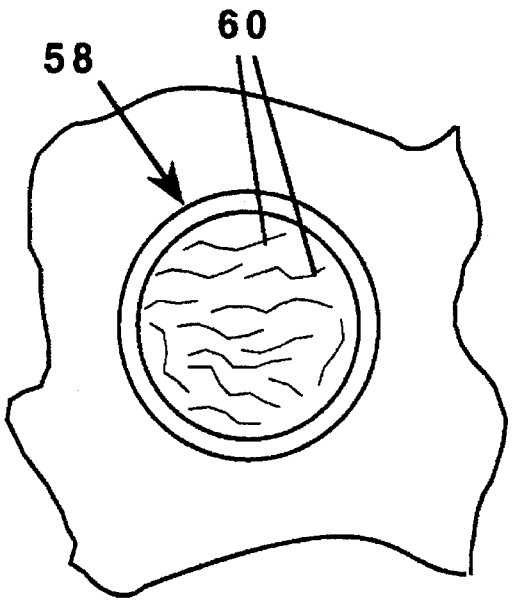

The liposome suspension may be sized, as by extrusion through a polycarbonate membrane or the like to reduce the largest liposomes to a desired upper size, e.g., 2–5 microns. Following this, the suspension may be further size fractionated, for example, by molecular sieve chromatography, to remove liposomes below a selected size range, e.g., 0.5 microns. At the same time, or in a separate step, the liposomes are separated from bulk-phase polymer material, to produce a suspension 58 of liposomes in a polymer-free aqueous medium, as shown in FIG. 14B.

Figure 14D:
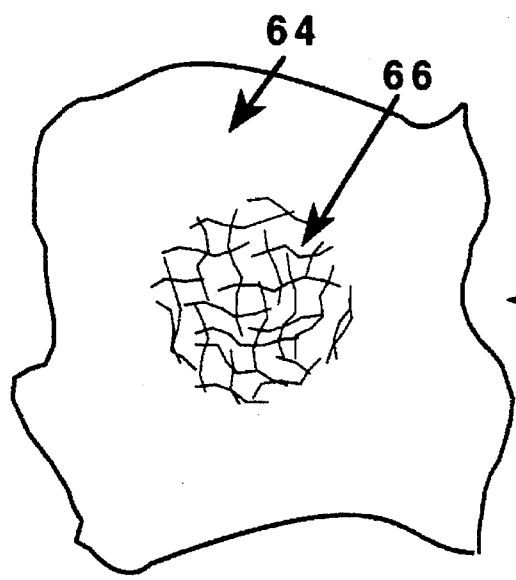
Figure 14C:
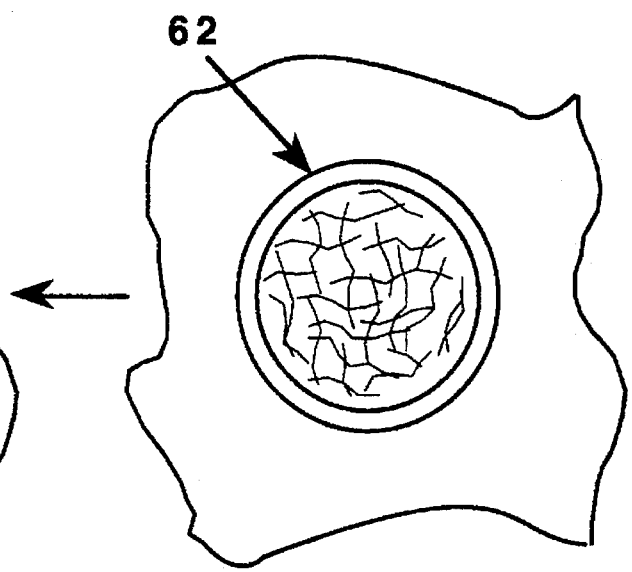

The liposome suspension is now subject to heat or irradiation treatment to initiate crosslinking of the encapsulated polymer suspension, as shown in FIG. 14C, according to standard methods such as outlined above. The cross-linked matrices, such as matrix 62, have the approximate sizes of the encapsulating liposomes.

In the final step, shown in FIG. 14D, the suspension is treated to remove the encapsulating liposome membranes, leaving a suspension 64 of the crosslinked particles, such as particle 66. Membrane dissolution may be produced by detergents, organic solvents, or the like. The microparticles may be separated from the lipid and lipid-solvent components by filtration or the like, then resuspended in an aqueous medium for further processing.

5. Gelatin Dispersion

This is a specific embodiment of a more general approach in which the polymer filaments or monomer subunits used in forming the microparticles are mixed with a suspension of proteins, such as agar, gelatin, or albumin (Kreuter, Tanaka). The mixture is then dispersed under conditions effective to produce desired sized particles containing the mixture components. In the case of gelatin containing particles, the mixture may be cooled during the dispersion process to produce gelled particles having a desired size.

The particles are then treated under polymerization and/or crosslinking conditions, preferably under conditions that do not also lead to crosslinking of gelatin molecules to the polymer structure. After microparticle formation, the gelatin molecules may be removed from the structure, with such in a decondensed form, e.g., by heating the material or enzymatic digestion.

Other methods for forming microparticles have been reported, and are contemplated herein for use in preparing charged-polymer microparticles having the properties and characteristics discussed above.

III. Switching Device

The invention includes a switching device that utilizes the condensation-decondensation and/or diode properties of a polymer-matrix microparticle of the type described above, operated in an asymmetric electric field.

The device is designed for use with a voltage source and generally includes a polymer-matrix microparticle of the type described above, a first chamber containing an electrolyte medium that is in contact with an interior surface region of the microparticles' surface, a second chamber containing an electrolyte medium that is in contact with an exterior surface region of the microparticles' surface, and electrical connections adapted to connect the electrolyte medium in the chambers to the voltage source, for applying a voltage having a selected voltage level and polarity across the microparticle.

As discussed above, the chambers are configured such that the interior surface region of the microparticle is substantially smaller than the microparticle's exterior surface region, preferably at least 25–100 times smaller. This yields the requisite field asymmetry for achieving the diode properties of the microparticle discussed above.

One preferred microparticle is composed of a sulfated, sulfonated, carboxylated, or phosphated anionic polymer filaments, preferably an anionic comb-polymer filament of the type described above.

The electrolyte solution in the two chambers preferably includes a multivalent ion species capable of maintaining the microparticle in a condensed state, in the absence of an applied electric field. These ions allow maximal changes in size between condensed and decondensed form, although they are not requisite for microparticle swelling and shrinking, nor for the microparticle diode behavior described above.

In the case of a microparticle formed of polyanionic filaments, the multivalent species are multivalent cations, such as calcium, histamine, magnesium, zinc, dionium, ethylenediamine, hexamethonium and decamethonium, and the trivalent cation lanthanum, while monovalent ions are not effective recondensing agents, effective to maintain the microparticle in its condensed state, in the absence of an applied negative electrical field. This concentration of multivalent cations is preferably in the range between about 1 and 100 mM.

At the same time, the concentration of monovalent cations in the solutions is preferably quite low, e.g., less than about 1 mM. Sodium chloride causes swelling of the particles when present at concentrations ranging from 0.1–10 mM.

As discussed above, applying a selected voltage potential across the microparticle is effective to induce a rapid voltage-dependent current which is severalfold greater, and can be up to two orders of magnitude or greater, than the current induced by applying a voltage having the opposite polarity. Also as discussed above, current flow may reach a half-maximal level in about 3–5 msec, and particle decondensation may occur with a half-maximal swelling with 200–300 msec.

In the devices described below, the microparticle is composed of anionic filaments, and so operates as a diode to allow current flow when an applied voltage has the negative-inside, positive-outside polarity as described with reference to FIG. 1. It will be appreciated that the polarity effects are reversed when the microparticle in the device is composed of cationic filaments.

A. Drug-Dispensing Device

FIG. 15A shows a miniature, implantable drug-dispensing device 70 constructed according to one embodiment of the invention. The device generally includes a housing 72 which encloses a chamber 73 containing a drug to be delivered. Drug is released from the chamber through an elastomeric tube 74 communicating the chamber with an drug outlet port (not shown).

Drug release from the device is controlled by decondensation of a microparticle 80, in accordance with the principles of the invention. To this end, the device includes a pair of chambers 76, 78 (FIGS. 15B, 15C), each containing an aqueous electrolyte solution, and a microparticle 80 disposed between the two chambers and providing an ion-flow barrier therebetween. The microparticle has the construction and properties described above.

With continued reference to FIGS. 15B and 15C, tube 74 in the device is disposed between particle 80 and an inner wall portion of chamber 78, such that the tube is in a relaxed "open" position when the particle is in a condensed state, as shown in FIG. 15B.

In the embodiment shown, the two chambers have the asymmetric configuration of the diode device described above in which the area of contact of the microparticle with the aqueous medium in chamber 76 is substantially less than that in chamber 78. Thus, when a voltage is applied across the two chambers, with the more negative voltage applied to chamber 76, the area of the microparticle exposed to the negative side of the field is substantially less than that exposed to the opposite, relatively positive side of the field.

The electric field is produced in the device by a battery 82 whose negative and positive terminals are connected to chambers 76, 78, respectively, through conductors 84, 86, respectively. Control of battery voltage to the chambers is controlled by an actuator 88 which is designed to alternately and recurrently connect the battery to the chambers.

In operation, the actuator in the device is set to a desired on/off schedule, and the device is implanted at a selected body site, e.g., at a subcutaneous site for slow drug release from the site. When the device is in a voltage-off condition, the microparticle in the device is in a condensed state, and tube 74 is open, as shown in FIG. 15B, allowing drug to be released by diffusion from the drug chamber.

When the device is switched to a voltage-on condition, the microparticle decondenses, forcing itself against the tube and partially or completely blocking a portion of the tube, to prevent drug escape from the device.

B. Diode Device

FIG. 16 shows a device 90 designed for use as a diode in an electrical circuit. The device includes a support 92 for a pair of chambers 94, 96, each containing an aqueous electrolyte solution, and a microparticle 98 disposed between the two chambers and providing an ion-flow barrier therebetween. The microparticle has the construction and properties described above.

The device includes electrodes 99, 100 in contact with the electrolyte solution in chambers 94, 96, respectively. The two electrodes are intended for connection to circuit elements (not shown) that are controlled by the diode, that is, which contain the diode in their circuit path.

In the embodiment shown, the two chambers have the asymmetric configuration of the diode device described above, such that when a voltage is applied across the two chambers, with the more negative voltage applied to chamber 94, the area of the microparticle exposed to the negative side of the field is substantially less than that exposed to the opposite, relatively positive side of the field.

In operation, the diode is placed in an electrical circuit designed to generate negative and positive voltages, for example, in an alternating current signal, across conductors 99, 100. When a positive voltage level is received, the microparticle remains in its condensed, high resistivity state, and current across the two chambers is substantially blocked. When a negative voltage level is received, the microparticle switches to a decondensed, low-resistivity state, allowing current flow across the two electrodes.

In one circuit mode, the device acts to rectify an alternative signal, imposing a phase transition, or lag time of the rectified signal of 3–5 msec. It is noted from the behavior of the microparticles discussed with reference to FIGS. 2A and 2B above, the rectification provided by the diode is voltage-dependent.

Since the response time of the device is in the 3–5 msec range, the signal frequency must be quite low, typically in the 10–200 Hz range, for rectification to occur. If the frequency of the signal is above about 200–400 Hz, the microparticle will not have time to respond to decondensing electrical fields, and the device will remain in a high-resistivity condition. The device may thus function as a band pass filter for low-frequency signals.

Alternatively, the diode can be used as a switching device for digital signals in a digital circuit. Here positive-voltage signals supplied to the device are effectively filtered, while negative-voltage signals are passed.

C. Sensor

FIG. 17 shows an optical sensor device 104 constructed according to another embodiment of the invention. The device includes a support 106 for a pair of chambers 108, 110, each containing an aqueous electrolyte solution, and a microparticle 112 disposed between the two chambers and providing an ion-flow barrier therebetween. The chambers have the general construction described above, and the microparticle has the composition and properties described above.

The device further includes a pair of electrodes 114, 116 which communicate with chambers 108, 110, respectively, and which are intended to be connected to circuit elements which supply negative or positive voltage signals across the electrodes. In this configuration, the device is identical in its construction and operation to diode device 90 described with respect to FIG. 16.

The present device additionally includes an optical detection unit 113 for measuring the opacity of microparticle 112 as the particle is switched between its condensed and decondensed states. The unit includes a photo source, such as an LED 115 powered by a voltage source, such as a battery 118. Light transmission through the microparticle is measured by a suitable photodetector, such as a PIN diode 120, which generate current signals through output connections 122, 124. That is, the condition of the diode, as evidenced by the opacity of the microparticle, is signaled at the two output connections.

The device is designed for use as a sensor of the environment of the microparticle. For example, since the response time of the microparticle will be temperature dependent, the ratio of resistivity response time/opacity response time can be calibrated as a function of temperature, to provide an accurate measure of temperature.

Alternatively, one of the two chambers may be provided with fluid inlet and outlet connections, such as those shown in dotted lines at 117, 119, respectively, for circulating an external test solution through the corresponding chamber. For example, for use in detecting a given ligand analyte, the microparticle may be constructed with ligand-binding receptors, as described above, such that binding of the ligand to the receptor will alter the switching condensation properties of the microparticles, as evidenced by a change in opacity of the microparticle in its condensed state.

Alternatively, for use as a pH sensor, the filament charge groups in the microparticle may be selected to have a $pK_H$ value in a critical pH range to be monitored, so that the charge-dependent condensation-decondensation properties of the microparticle will shift with changes in pH in that range, as detected by changes in the opacity of the microparticle.

It will be appreciated that the diode device shown in FIG. 16 may also be modified, as just described to operate as a sensing device, with changes in the properties of the microparticle, in response to changes in environmental conditions, being reflected by changes in measured diode-current levels.

D. Pump Device

FIG. 18A shows a miniature pump device 126 constructed according to another embodiment of the invention. The device includes a housing 128 which contains a pair of chambers 130, 132, each containing an aqueous electrolyte solution, and a microparticle 134 disposed between the two chambers and providing an ion-flow barrier therebetween. The chambers have the general construction described above, and the microparticle has the composition and properties described above.

The two chambers and microparticle are shown in enlarged scale in FIGS. 18B and 18C. As seen in these figures, the device also includes an elastomeric tube 136 disposed between the microparticle and a plate 138 supported in chamber 132. The tube acts to pump liquid between a pair of fluid reservoirs (not shown) as the tube is alternately and recurrently compressed (FIG. 18C) and relaxed (FIG. 18B), as the microparticle is alternately switched between decondensed and condensed conditions, respectively. The tube includes a one-way valve (not shown) to insure fluid movement in the tube in one direction only as the tube is compressed.

The electric field used for particle switching is produced in the device by a battery 140 whose negative and positive terminals are connected to chambers 130, 132, respectively, through conductors 142, 144, respectively. Supply of voltage to the chambers is controlled by an actuator 146 which receives signals through input leads 148, 150. The signals may activate an internally controlled voltage cycling, or may themselves provide the timing for the pump voltage cycling.

E. Mechanical Actuator

FIG. 19 shows a miniature mechanical actuator device 152 constructed according to another embodiment of the invention. The device includes a housing 154 containing a pair of chambers 156, 158, each containing an aqueous electrolyte solution, and a microparticle 160 disposed between the two chambers and providing an ion-flow barrier therebetween. The chambers have the general construction described above, and the microparticle has the composition and properties described above.

The device also includes a piston 162 supported on a pair of flexible membranes 164, 166 attached to the housing as shown. With the two membranes in a relaxed condition, the piston is held at an axial position which lust places a pusher plate 168 on the piston in contact with the microparticle, with such in its relaxed condition. When the microparticle is decondensed, by applying a negative electric across the chambers, the expanded particle pushes plate 168 and piston 162 to the right in the figure.

Also included in the device is a battery 170 whose positive and negative terminals are connected electrically to the two chambers as shown. Supply of voltage to the chambers is controlled by an actuator 172 which receives signals through input leads 174, 176.

In operation, the device is held in a fixed position, the distal end of piston 162 is connected to the object to be acted upon, e.g., a moving part in a miniature mechanical apparatus. To activate movement of the piston and its attached object, an electrical signal is supplied to actuator 172, to connect the battery to the two chamber electrodes, and cause the microparticle to decondense.

Alternatively, the device may be directly activated by supplying negative voltage signals directly from controlling circuit elements to the chambers, bypassing the battery circuit.

It will be appreciated from the forgoing that a variety of other mechanical and electrical switching devices may be constructed around the microparticle switching element described in the above devices. These devices will have common advantages of: (a) miniaturization, (b) rapid response times, (c) simple mechanical structure, and (d) low power requirements.

The following examples illustrate methods for isolating and demonstrating certain diode and condensation-decondensation properties of microparticles constructed in accordance with the invention.

EXAMPLE 1

Isolation of Mast Cells

Mast cell secretory granules were prepared from adult beige ($bg^j/bg^j$) mice (Jackson Laboratories, Bar Harbor, Me.) according to standard methods described by Monck et al., (1991), and modified to increase the number of intact isolated secretory granules. Cells were obtained by peritoneal lavage with a solution of the following composition (in mM): 136 NaCl, 1 $MgCl_2$, 2 $CaCl_2$, 22 $NaHCO_3$, 0.4 $K_2HPO_4$, 2 Glucose, 8.8 units/ml Heparin, 0.1% Bovine serum albumin (300 mOsm/kg, pH 7.3). Cells were resuspended in 1 ml, layered on 2 ml 22.5% wt/vol metrizamide and centrifuged at room temperature for 20 min. at 400 g. The pellet was resuspended in 1 ml of a $Ca^{2+}$, $Mg^{2+}$-free sonication buffer of the following composition (in mM): 130 NaCl, 10 KCl, 22 $NaHCO_3$, 0.3 $K_2HPO_4$, 0.1% Bovine serum albumin (300 Mosm/kg, pH 7.3). This suspension of purified mast cells was subjected to 4 sonication pulses at 25% of maximum power (sonicator model 45; Branson Sonic Power Co., Danbury, Conn.) and plated onto glass bottomed chambers and stored at 37° C. under 5% $CO_2$ atmosphere until use. An average of about 200 intact secretory granules per mouse were routinely obtained, that were osmotically stable with a half-life of over 3h.

Isolated secretory granules were bathed in a standard solution containing (in mM): 25 NaCl, 125 Kcl, 2 $CaCl_2$, 1 $MgCl_2$, 0.2 ATP, 10 HEPES (300 Mosm/kg, pH 7.3).

Alternatively, mast cells were collected in a solution containing 150 mM NaCl, 10 mM Hepes, 3 mM KOH, 0.943 mM NaOH, 1 mM $MgCl_2$, 2 mM $CaCl_2$, and 12 mM glucose, 310 mmol/kg, pH 7.3, at room temperature. Secretion was stimulated by 10 ug/ml of compound 48/80 (Sigma Chemical Co., St. Louis, Mo.). Swelling of secretory granules was recorded using a Toshiba video camera (model IKC30M) mounted on an IM35 microscope (Zeiss) equipped with Nomarski optics including a 63× oil immersion Zeiss objective. (3500×, final magnification). The diameter of the granules was measured by single frame video image analysis at a sample rate of 30 frames/sec. Single frame images were played back from a VCR (BV-1000 Mitsubishi) and sampled by a frame grabber (DT 2851, Data Translation) operated by the Image-Pro software package (Media Cybernetics). Volumetric expansion was calculated assuming a spherical shape for the secretory granules. Size is conveniently expressed as a percent of final decondensed volume after exocytosis in external solution (pH 7.3). Granules were re-condensed to within 5% of pre-secretion volume by bathing in a solution containing 50 mM histamine, pH 3, devoid of other ions.

EXAMPLE 2

Diode Measurements on Microparticles

Granule matrices, devoid of granular membrane, were recondensed by exposure to an acidic histamine-containing solution.

Glass pipettes (Kimax-100) were pulled on a horizontal puller (LM-3P/A; Adams and List, Great Neck, N.Y.) and had resistances between 5 and 15 million Ohms (MOhms) in the histamine solutions used. Isolated granule matrices were inserted into the pipette by applying suction. Unless otherwise specified, the solution in both the bath and the pipette contained (in mM) 12 $HisCl_2$, 0.5 citric acid, pH 3.5. A current to voltage converter, with a gain of 1.2 millivolt/ nanoamper (Mv/Na), followed by a unity gain differential amplifier is used to control the pipette potential. An IDA interface (INDEC Systems, Sunnyvale, Calif.) with a COMPAQ 386-25 computer and the CCLAMP software (INDEC Systems) is used to apply the voltages and sample the currents every 2.5 ms.

For measuring the swelling, isolated granule matrices were imaged as described previously. The IMAGEPRO software (Media Cybernetics, Silver Spring, Md.) is used to measure granule cross-sectional area. Relative swelling was calculated as $A_t A_o$ where $A_t$=the cross-sectional area at an arbitrary time and $A_o$=the cross-sectional area 165 ms before the onset of the voltage. The data shown here corresponds to the swelling of a single granule matrix in response to a single voltage pulse. Cross-sectional areas for each frame were measured seven times. Each data point represents the mean ±S.D. of the seven measurements.

To measure the force exerted by a swollen granule, a condensed granule was brought near a stress transducing beam (Akers, Senso-nor, Norway) which consisted of two active resistors whose resistance changed upon bending of the beam. These resistors formed two legs of a Wheatstone bridge while two passive resistors made up the remaining two legs. The voltage across the diagonal of the Wheatstone bridge is measured. This voltage was zero when the bridge was balanced. When the beam was bent, due to granule swelling for instance, the resistance of the active resistors changed, unbalancing the bridge and resulting in a voltage proportional to the bending. The voltage was filtered (bandpass filter, corner frequencies 0 and 3 Hertz (Hz)), amplified ($10^5$×) and sampled by the computer every 6.36 ms. The transducer was calibrated by placing a known weight at its edge and measuring the resulting voltage across the Wheatstone bridge.

A condensed matrix core from the secretory granule of a beige mouse mast cell was sealed against the tip of a glass pipette. The potential at the pipette tip was controlled by a current to voltage converter.

EXAMPLE 3

Decondensation Measurements on Microparticles

Isolated biopolymer particles were isolated from beige mouse mast cells as described in Example 1. Particles were imaged by videomicroscopy at approx. 3,500 magnification with a Zeiss (IM35) inverted microscope equipped with Normarski optics. Expansion of the particle was monitored using a video camera (model 1KC30M; Toshiba, Japan) and recorded at 30 frames/sec on a video recorder (BV-1000; Mitsubishi, Japan). The diameter of the particles was measured by single frame video image analysis. Digital image analysis was implemented using a frame grabber (DT 2851; Data Translation, Marlboro, Mass.) installed on a microcomupter (AT-286; Beltron, Feasterville, Pa.) operated by IMAGEPRO software (Media Cybernetics, Silver Spring, Md.) to measure granule cross-sectional area.

Volumetric expansion was calculated assuming a spherical shape for the secretory granules or particles. Relative swelling was calculated as $A_t A_o$ where $A_t$=the cross-sectional area at an arbitrary time and $A_o$=the cross-sectional area 165 ms before the onset of the voltage. The data shown in FIG. 6 corresponds to the swelling of a single granule matrix in response to a single voltage pulse. Cross-sectional areas for each frame were measured seven times. Each data point represents the mean ±S.D. of the seven measurements.

EXAMPLE 4

Measurement of Force generation by Microparticles

To measure the force exerted by a particle during expansion, a condensed matrix core from the secretory granule of a beige mouse mast cell was sealed against the tip of a glass pipette. The potential at the pipette tip was controlled by a current to voltage converter, as described in Example 2. The particle was positioned adjacent a stress transducing beam (Akers, Senso-nor, Norway) which consisted of two active resistors whose resistance changed upon bending of the beam. These resistors formed two legs of a Wheatstone bridge while two passive resistors made up the remaining two legs. The voltage across the diagonal of the Wheatstone bridge was measured. This voltage was zero when the bridge was balanced.

A +8 V potential was applied to the particle, resulting in swelling of the particle. This swelling caused the transducing beam to bend, and the resistance of the active resistors in the transducing element changed, unbalancing the bridge, and producing a voltage proportional to the bending. The voltage was filtered (bandpass filter, corner frequencies 0 and 3 Hertz (Hz)), amplified ($10^5$×) and sampled by the computer every 6.36 ms. Results of this experiment are shown in FIG. 10. The transducer was calibrated by placing a known weight at its edge and measuring the resulting voltage across the Wheatstone bridge.

Although the invention has been described with reference to specific embodiments, it will be appreciated that various changes and modifications may be made without departing from the invention.

It is claimed:

1. A switching device for use with a voltage source effective to generate a voltage having a selected polarity, comprising a polymer-matrix microparticle composed of a matrix of crosslinked polyionic polymer filaments and defining a surface, a first chamber containing an electrolyte medium that is in contact with an interior surface region of said surface, a second chamber containing an electrolyte medium that is in contact with an exterior surface region of said surface, said first chamber and said second chamber being configured such that said interior surface region is substantially less than said exterior surface region, and electrical connections adapted to connect the electrolyte medium to such a voltage source, for applying across said first chamber and said second chamber, a voltage having a selected voltage level and polarity, whereby the device allows electric current flow between the first chamber and the second chamber when the voltage has one of two possible polarities, and substantially blocks current flow between the first chamber and the second chamber the other of two possible polarities.

2. The switching device of claim 1, wherein said first chamber and said second chamber are separated by an opening defining an interior solid angle and an exterior solid angle subtending interior and exterior sides of the opening, respectively, and said interior solid angle is substantially less than said exterior solid angle.

3. The switching device of claim 2, wherein application of a given voltage causes the electric current flow to reach a half-maximal value, for the given voltage, within about 30 msec of said application, when the voltage applied is between ±0.5 to 5 volts.

4. The switching device of claim 2, for use as a miniature, implantable drug-delivery device for dispensing a drug, which further includes a drug reservoir having a flexible drug-outlet tube which is open when the polymer-matrix microparticle is in its condensed condition and closed when the polymer-matrix microparticle is in its decondensed condition.

5. The switching device of claim 2, for use as a miniature pump, which further includes a flexible pumping tube which is alternately squeezed and released as the polymer-matrix microparticle is switched between its decondensed and condensed states, respectively.

6. The switching device of claim 1, wherein said interior surface region is at least 25 times that of the exterior surface region.

7. The switching device of claim 1, wherein the electrolyte medium contains a multivalent solute species effective to condense said polymer-matrix microparticle, in the absence of an electric field, and said polymer-matrix microparticle is decondensed in the presence of a voltage whose polarity is effective to allow electric current flow.

8. The switching device of claim 7, wherein said polymer-matrix microparticle has a dimension between about 0.5 and 5.0 μm.

9. The switching device of claim 1, wherein the crosslinked polyionic polymer filaments forming the matrix are polyanionic polymer filaments.

10. The switching device of claim 9, wherein the crosslinked polyionic polymer filaments forming the matrix are sulfated, sulfonated, carboxylated, or phosphated filaments.

11. The switching device of claim 10, wherein the matrix is composed of crosslinked comb-polymer glycoproteins.

* * * * *